(12) United States Patent
Frisken et al.

(10) Patent No.: US 11,730,362 B2
(45) Date of Patent: Aug. 22, 2023

(54) OPTICAL COHERENCE METROLOGY AND TOMOGRAPHY WITH IMPROVED REGISTRATION

(71) Applicant: Cylite Pty Ltd, Notting Hill (AU)

(72) Inventors: Steven James Frisken, Vaucluse (AU); Grant Andrew Frisken, Mitcham (AU)

(73) Assignee: Cylite Pty Ltd, Notting Hill (AU)

( * ) Notice: Subject to any disclaimer, the term of this patent is extended or adjusted under 35 U.S.C. 154(b) by 0 days.

(21) Appl. No.: 17/497,083

(22) Filed: Oct. 8, 2021

(65) Prior Publication Data
US 2022/0047156 A1  Feb. 17, 2022

Related U.S. Application Data

(63) Continuation of application No. 16/481,478, filed as application No. PCT/AU2018/050038 on Jan. 20, 2018, now Pat. No. 11,166,630.

(30) Foreign Application Priority Data

Jan. 28, 2017  (AU) .............................. 2017900245

(51) Int. Cl.
*A61B 3/10* (2006.01)
*G06T 7/33* (2017.01)

(52) U.S. Cl.
CPC ................ *A61B 3/102* (2013.01); *G06T 7/33* (2017.01); *G06T 2207/10101* (2013.01)

(58) Field of Classification Search
None
See application file for complete search history.

(56) References Cited

U.S. PATENT DOCUMENTS

| 4,747,683 A | 5/1988 | Doane |
| 5,861,955 A | 1/1999 | Gordon |

(Continued)

FOREIGN PATENT DOCUMENTS

| EP | 1602320 A1 | 12/2005 |
| WO | 2010011656 A1 | 1/2010 |

(Continued)

OTHER PUBLICATIONS

Extended European Search Report received in corresponding European Application No. 19814657.3 dated Jul. 12, 2021.

(Continued)

*Primary Examiner* — Delomia L Gilliard
(74) *Attorney, Agent, or Firm* — Mattingly & Malur, PC

(57) ABSTRACT

Methods and apparatus are provided for optical coherence metrology or tomography across an extended area of an eye with improved registration. At least two optical coherence tomograms are acquired, with each tomogram containing data from regions of an anterior surface of the eye that are at least partially overlapping, and data from one or more deeper structures such as the retina or the anterior or posterior lens surfaces. The tomograms are then processed to register the data from the overlapping portions of the anterior surface regions, thereby registering the data from the deeper structures. In certain embodiments the reference arm of the apparatus comprises a compound reflector having at least two axially separated reflective surfaces for applying differential delays to different portions of the reference beam. The depth of field of the apparatus is thereby extended to enable measurement of eye length. In certain embodiments eye length measurements at a number of angles of incidence provide information on total eye shape.

20 Claims, 14 Drawing Sheets

(56) References Cited

U.S. PATENT DOCUMENTS

| | | |
|---|---|---|
| 6,454,761 B1 | 9/2002 | Freedman |
| 7,800,759 B2 | 9/2010 | Lai et al. |
| 7,982,881 B2 | 7/2011 | Fercher |
| 8,534,838 B2 | 9/2013 | Barth |
| 9,668,647 B2 | 6/2017 | Grenon et al. |
| 2003/0030915 A1 | 2/2003 | Amin |
| 2006/0066869 A1 | 3/2006 | Ueno et al. |
| 2006/0072424 A1* | 4/2006 | Everett .............. G01B 9/02069 369/44.11 |
| 2007/0273957 A1 | 11/2007 | Zalevsky |
| 2010/0033727 A1* | 2/2010 | Ko .................... G01B 9/02028 356/451 |
| 2011/0273669 A1 | 11/2011 | Abitbol et al. |
| 2012/0140173 A1 | 6/2012 | Uhlhorn |
| 2013/0182218 A1 | 7/2013 | Naba |
| 2013/0216115 A1 | 8/2013 | Iwase |
| 2013/0242259 A1 | 9/2013 | Hacker |
| 2014/0160430 A1* | 6/2014 | Ko ...................... G01B 9/0201 351/206 |
| 2016/0135679 A1* | 5/2016 | Frisken ................... A61B 3/14 351/212 |
| 2016/0135680 A1 | 5/2016 | Anderson |
| 2016/0345820 A1* | 12/2016 | Frisken ................ A61B 3/0025 |
| 2020/0103215 A1 | 4/2020 | Frisken |

FOREIGN PATENT DOCUMENTS

| | | |
|---|---|---|
| WO | 2011060356 A1 | 5/2011 |
| WO | 2011121959 A2 | 10/2011 |
| WO | 2011155150 A1 | 12/2011 |
| WO | WO-2011155150 A1 * | 12/2011 .......... A61B 3/0025 |
| WO | 2014020597 A1 | 2/2014 |
| WO | 2016094940 A1 | 6/2016 |

OTHER PUBLICATIONS

Dolgin "The myopia boom" Nature 519, 276-278 (Mar. 19, 2015).
Atchison et al. "Eye shape in emmetropia and myopia" Investigative Ophthalmology & Visual Science 45(10) 3380-3386 (Oct. 2004).
Extended European Search Report received in corresponding European Application No. 21182312.5 dated Nov. 12, 2021.

* cited by examiner

OPTICAL COHERENCE METROLOGY AND TOMOGRAPHY WITH IMPROVED REGISTRATION

FIELD OF THE INVENTION

The invention relates to apparatus and methods for ocular metrology, in particular for measuring the shape of the human eye using optical coherence tomography (OCT) techniques. However it will be appreciated that the invention is not limited to this particular field of use.

RELATED APPLICATIONS

The present application claims priority from Australian Provisional Patent Application No 2017900245 entitled 'Optical Coherence Metrology and Tomography with Improved Registration' filed on 28 Jan. 2017, the contents of which are incorporated herein by reference.

BACKGROUND OF THE INVENTION

Any discussion of the prior art throughout the specification should in no way be considered as an admission that such prior art is widely known or forms part of the common general knowledge in the field.

Measurement of many if not all of the optical surfaces in the human eye, as well as total eye shape, provides important information about the progression of various diseases and conditions. In particular, myopia development has become an area of specific interest due to the rapidly escalating incidence of myopia particularly in eastern Asia. In a Nature news feature entitled 'The Myopia Boom', E. Dolgin, Nature 519, 276-278, March 2015, it was reported that the incidence of myopia (i.e. short-sightedness) in China has risen in sixty years from less than 20% of the population to around 90% of young adults and teenagers. The condition can lead to deformation and thinning of the inner parts of the eye, increasing the incidence of retinal detachment, cataracts, glaucoma and blindness. The gold standard for the challenging task of measuring total eye shape is magnetic resonance imaging (MRI), described for example in Atchison et al 'Eye Shape in Emmetropia and Myopia' (Investigative Ophthalmology & Visual Science 45(10), 3380-3386, October 2004). However MRI requires high cost, complex equipment and lacks the accuracy required to track small developmental changes over periods of weeks and months.

It would be attractive to use optical techniques for measuring eye shape. Optical coherence tomography (OCT) is a widely used interferometric technique for studying biological samples including in vivo tissue such as the human eye, with lateral and depth resolution, using information contained within the amplitude and phase of reflected or scattered light. While spectral domain OCT has proved effective at providing measurements of various ocular layers and depths, for a number of reasons existing OCT techniques are not well suited for obtaining accurate information on total eye shape. Among these reasons is a difficulty in measuring eye length, defined as the distance between the corneal apex and the fundus, in a single exposure. This is because its magnitude, generally around 20 mm in an adult human, significantly exceeds the depth of field or Nyquist range of typical spectral domain OCT systems. The measurement depth of field Z for a system having a detector array with N pixels or photodiodes in the dispersion direction and a light source with centre wavelength $\lambda$ and half width $\Delta\lambda$, is given by $Z=N\oplus\lambda^2/(4\oplus\Delta\lambda)$. A system with N=1000, $\lambda$=840 nm and $\Delta\lambda$, =40 nm would therefore have a measurement depth of field of about 4.4 mm, much less than the typical eye length. A fundamental problem is that a broad source bandwidth, i.e. large $\Delta\lambda$, is required to provide the short coherence length necessary for depth resolution, but for a given detector array this limits the depth range over which the sample beam can interfere with the reference beam.

U.S. Pat. No. 7,982,881 entitled 'Apparatus and method for interferometric measurement of a sample' discloses several techniques for extending the axial depth of an OCT system by providing multiple reference paths that can be interfered with light reflected from different depths of an eye. This allows axial measurements of a number of points at different depths to be made. However due to the maximum exposure limits in a clinical setting, or limitations in the available optical power, it is not always possible to obtain measurements over time periods sufficiently short to preclude eye movement, i.e. less than a few milliseconds. This is particularly important when relative accuracy between many transverse sampling points of the order of a few microns or less is required. The 2881 patent doesn't provide any guidance as to how a high signal to noise ratio measurement can be achieved when sampling over a large area of the eye, as it is not possible to compute from the limited acquired data set the lateral and axial position of the eye to co-register accurately the lateral and axial on-eye locations of the various enhanced axial scans which are described. Consequently, several important optical properties of the eye cannot be calculated from the obtained set of axial scans. For example when planning intra-ocular lens (IOL) surgery it is often advantageous to know accurately the optical power and astigmatism of the front and back corneal surfaces, as well as the axial length and lens thickness and curvature.

U.S. Pat. No. 8,534,838 entitled 'Optical coherence reflectometry with depth resolution' describes an apparatus that uses a 'double-refracting optical system' designed to project a line focus onto both the front of the eye and the retina at the same time, and similarly to project the line focus into two reference paths of different lengths. All four of the returning line foci are combined, passed through a slit aperture to reject stray light then dispersed onto a 2-D sensor array. The 'double-refracting optical system' can be polarisation-based, e.g. using a birefringent lens, or diffraction-based, e.g. using a diffractive optical system. Although a line scan system allows some capability for locating the position of the scan on the cornea in one axis it is not possible to ensure the position of the slice unambiguously for registration of a series of slices to build a more complete correctly registered image of the optical interfaces in the eye. Additionally the slit aperture is able to provide a high-resolution axial scan but does not provide a means to remove crosstalk from different lateral positions. In particular, in regions where high intensity specular reflection transitions to low intensity scattering as occurs on the human cornea, it is difficult to prevent lateral crosstalk from high intensity regions overwhelming and corrupting the results from neighbouring points at different depths. It would be advantageous therefore to provide a method of registration that overcomes the crosstalk limitations by providing aperturing around the points of interest, and also to provide a three-dimensional grid of points for registration so that a high signal to noise image can be constructed.

The ability of OCT to measure total eye shape is also compromised by the eye's focusing power. For example an array of beamlets established to measure with lateral resolution features at the back of the eye, e.g. the retina, are not appropriate for creating a map of features at the front of the eye, e.g. the cornea. To form a small beamlet at the retina it is necessary to illuminate the cornea with a collimated beam, which lacks the precision to map the front surface of the eye. Furthermore an array of parallel beamlets used to measure anterior portions of the eye will be focused onto one region of the retina, and therefore can't provide a topographic map of the back of the eye. An additional difficulty for using OCT to measure eye shape is that the apparent curvature of the retina is influenced by the position of the OCT instrument relative to the eye. There is a need therefore for improved OCT systems and methods for measuring total eye shape.

Unless the context clearly requires otherwise, throughout the description and the claims the words 'comprising', 'comprises' and the like are to be construed in an inclusive sense as opposed to an exclusive or exhaustive sense. That is, they are to be construed in the sense of 'including, but not limited to'.

OBJECT OF THE INVENTION

It is an object of the present invention to overcome or ameliorate at least one of the limitations of the prior art, or to provide a useful alternative. It is an object of the present invention in a preferred form to provide spectral domain OCT apparatus and methods with the ability to measure total eye shape. It is another object of the present invention in a preferred form to provide spectral domain OCT apparatus and methods for ocular metrology or tomography with improved registration.

SUMMARY OF THE INVENTION

According to a first aspect of the present invention there is provided a method for performing optical coherence metrology across an extended area of an eye, said method comprising the steps of:
(i) acquiring, within a single frame of a two-dimensional sensor array, a first optical coherence tomogram of said eye, said first optical coherence tomogram containing data from a first region of an anterior surface of said eye, and data from a third region of said eye;
(ii) acquiring, within a single frame of said two-dimensional sensor array, a second optical coherence tomogram of said eye, said second optical coherence tomogram containing data from a second region of said anterior surface that is at least partially overlapping with said first region, and data from a fourth region of said eye; and
(iii) processing the first and second optical coherence tomograms to register the overlapping portions of the first and second regions of said anterior surface, thereby registering the data from the third and fourth regions of said eye.

Preferably, at least one of the first and second regions of the anterior surface includes a portion of the anterior sclera. More preferably, at least one of the first and second regions of the anterior surface includes a portion of the limbus.

Each of the first and second optical coherence tomograms is preferably acquired within a time period of 2 milliseconds or less, more preferably within a time period of 1 millisecond or less, and even more preferably within a time period of 100 microseconds or less.

Each of the first and second optical coherence tomograms preferably contains data from a plurality of discrete points within the respective region of the anterior surface. In certain embodiments each of the third and fourth regions of the eye comprises a region of the retina. In other embodiments each of the third and fourth regions of the eye comprises a plurality of discrete points on the retina.

In certain embodiments the position of an apparatus used to acquire the first and second optical coherence tomograms is adjusted relative to the eye between the acquisition of the first optical coherence tomogram and the acquisition of the second optical coherence tomogram. In other embodiments an internal delay in an apparatus used to acquire the first and second optical coherence tomograms is adjusted between the acquisition of the first optical coherence tomogram and the acquisition of the second optical coherence tomogram. In yet other embodiments one or more lenses in an apparatus used to acquire the first and second optical coherence tomograms are changed between the acquisition of the first optical coherence tomogram and the acquisition of the second optical coherence tomogram.

In certain embodiments the method further comprises the step of imposing a predetermined optical path length difference on first and second laterally spaced portions of a reference beam or a sample beam when acquiring at least one of the first and second optical coherence tomograms, and wherein the processing step further comprises taking into account the predetermined optical path length difference. The predetermined optical path length difference is preferably imposed on first and second laterally spaced portions of a reference beam. More preferably, the predetermined optical path length difference is imposed by a compound reflector having first and second axially separated reflective surfaces for reflecting the first and second laterally spaced portions of the reference beam.

According to a second aspect of the present invention there is provided an apparatus for performing optical coherence metrology across an extended area of an eye, said apparatus comprising:
an interferometer for acquiring, each within a single frame of a two-dimensional sensor array, first and second optical coherence tomograms of an eye, said first optical coherence tomogram containing data from a first region of an anterior surface of said eye and data from a third region of said eye, and said second optical coherence tomogram containing data from a second region of said anterior surface and data from a fourth region of said eye, wherein said first and second regions are at least partially overlapping; and
a computer for processing the first and second optical coherence tomograms to register the overlapping portions of the first and second regions of said anterior surface, thereby registering the data from the third and fourth regions of said eye.

Preferably, the interferometer is configured such that, in use, at least one of the first and second regions of the anterior surface includes a portion of the anterior sclera. More preferably, the interferometer is configured such that, in use, at least one of the first and second regions of the anterior surface includes a portion of the limbus. In certain embodiments the interferometer is configured such that, in use, each of the third and fourth regions of the eye comprises a region of the retina.

The apparatus is preferably configured such that each of the first and second optical coherence tomograms can be acquired within a time period of 2 milliseconds or less, more preferably within a time period of 1 millisecond or less, and even more preferably within a time period of 100 microseconds or less.

Preferably, the interferometer comprises a spatial sampling element for providing an array of beamlets, such that, in use, each of the first and second optical coherence tomograms contains data from a plurality of discrete points within the respective region of the anterior surface. In certain embodiments the spatial sampling element is configured to provide focusing of different beamlets at different depths in the eye. The spatial sampling element preferably comprises a two-dimensional lenslet array. In certain embodiments the apparatus further comprises a structured aperturing partition for suppressing crosstalk between beamlets returning from the eye. The structured aperturing partition preferably comprises a first member having a plurality of apertures for passing on-axis beamlets returning from the eye. More preferably, the structured aperturing partition comprises a second member extending substantially parallel to the propagation direction of the on-axis beamlets for suppressing the passage of off-axis light. In certain embodiments the interferometer and the spatial sampling element are configured such that, in use, each of the third and fourth regions of the eye comprises a plurality of discrete points on the retina.

In certain embodiments the interferometer comprises one or more lenses adapted to be interchanged between the acquisition of the first optical coherence tomogram and the acquisition of the second optical coherence tomogram.

In certain embodiments the interferometer comprises a multi-length delay element for imposing a predetermined optical path length difference on first and second laterally spaced portions of a reference beam or a sample beam when acquiring at least one of the first and second optical coherence tomograms, and wherein the computer is configured to take into account the predetermined optical path length difference when processing the respective optical coherence tomogram. The multi-length delay element is preferably configured to impose the predetermined optical path length difference on first and second laterally spaced portions of a reference beam. More preferably, the multi-length delay element comprises a compound reflector having first and second axially separated reflective surfaces for reflecting the first and second laterally spaced portions of the reference beam. In preferred embodiments the compound reflector comprises a medium selected to have a dispersion that at least partially compensates for the dispersion of the eye. Preferably, the compound reflector is selected such that the predetermined optical path length difference substantially compensates for the axial depth of the eye.

According to a third aspect of the present invention there is provided a method for measuring eye shape, said method comprising the steps of:
  (i) measuring, in a first acquisition, the anterior segment of an eye and the axial depth of said eye using an optical coherence tomography apparatus having a first optical relay;
  (ii) calculating, from data obtained in said first acquisition, refractive properties of the anterior segment of said eye;
  (iii) capturing, in a second acquisition, an image of the retina of said eye over a grid of points using said optical coherence tomography apparatus having a second optical relay that is calibrated to said first optical relay;
  (iv) determining the axial and angular positions of said second acquisition relative to said first acquisition; and
  (v) determining a corrected retinal shape based on a correction formula or through use of an optical model, using the calculated refractive properties of the anterior segment of said eye.

Preferably, the anterior segment is measured simultaneously over a grid of points in the first acquisition. The axial depth is preferably measured to the retinal pigment epithelium at the fovea of the eye. Preferably, the fovea of the eye is identified from the image of the retina.

According to a fourth aspect of the present invention there is provided an optical coherence tomography apparatus for measuring eye shape, said apparatus being configured to:
  measure, in a first acquisition using a first optical relay, the anterior segment of an eye and the axial depth of said eye;
  calculate, from data obtained in said first acquisition, refractive properties of the anterior segment of said eye;
  capture, in a second acquisition using a second optical relay that is calibrated to said first optical relay, an image of the retina of said eye over a grid of points;
  determine the axial and angular positions of said second acquisition relative to said first acquisition; and
  determine a corrected retinal shape based on a correction formula or through use of an optical model, using the calculated refractive properties of said anterior segment of said eye.

The apparatus is preferably configured to measure the anterior segment simultaneously over a grid of points in the first acquisition. Preferably, the apparatus is configured to measure axial depth to the retinal pigment epithelium at the fovea of the eye. The apparatus is preferably configured to identify the fovea of the eye from the image of the retina.

According to a fifth aspect of the present invention there is provided a method for performing optical coherence metrology or tomography of a sample, said method comprising the steps of:
  (i) splitting light from an optical source into a sample beam and a reference beam;
  (ii) imposing on first and second laterally spaced portions of said sample beam or said reference beam a predetermined optical path length difference;
  (iii) directing said sample beam onto said sample for interaction with first and second axially separated regions of said sample, and collecting light reflected from or transmitted through the first and second axially separated regions of said sample;
  (iv) mixing said reference beam with the reflected or transmitted light;
  (v) detecting an interference signal resulting from the mixing of the reference beam with the reflected or transmitted light; and
  (vi) processing the detected interference signal to provide an optical coherence tomogram of said sample,
  wherein said predetermined optical path length difference at least partially compensates for the axial separation between the first and second regions of said sample.

Preferably, the sample beam comprises an array of beamlets for interaction with a plurality of discrete points within the first or second regions of the sample. The predetermined optical path length difference is preferably imposed on first and second laterally spaced portions of the reference beam. More preferably, the predetermined optical path length difference is imposed by a compound reflector having first and second axially separated reflective surfaces for reflecting the first and second laterally spaced portions of the reference beam.

According to a sixth aspect of the present invention there is provided an apparatus for performing optical coherence metrology or tomography of a sample, said apparatus comprising:
  an optical source;
  an interferometer for:

splitting light from said optical source into a sample beam and a reference beam;

directing said sample beam onto a sample for interaction with first and second axially separated regions of said sample, and collecting light reflected from or transmitted through the first and second axially separated regions of said sample; and mixing said reference beam with the reflected or transmitted light;

a detector for detecting an interference signal resulting from the mixing of the reference beam with the reflected or transmitted light;

a multi-length delay element for imposing on first and second laterally spaced portions of said sample beam or said reference beam, a predetermined optical path length difference; and a processor for processing the detected interference signal to provide an optical coherence tomogram of said sample, wherein said multi-length delay element is selected such that said predetermined optical path length difference at least partially compensates for the axial separation between the first and second regions of said sample.

The apparatus preferably comprises a spatial sampling element for generating from the sample beam an array of beamlets for interaction with a plurality of discrete points within the first or second regions of the sample. Preferably, the spatial sampling element comprises a lenslet array. In preferred embodiments the multi-length delay element is configured to impose the predetermined optical path length difference on first and second laterally spaced portions of the reference beam. Preferably, the multi-length delay element comprises a compound reflector having first and second axially separated reflective surfaces for reflecting the first and second laterally spaced portions of the reference beam. The multi-length delay element preferably comprises a medium selected to have a dispersion that at least partially compensates for the dispersion of the sample.

According to a seventh aspect of the present invention there is provided an article of manufacture comprising a computer usable medium having a computer readable program code configured to implement the method according to the first, third or fifth aspects, or to operate the apparatus according to the second, fourth or sixth aspects.

BRIEF DESCRIPTION OF THE DRAWINGS

Preferred embodiments of the invention will now be described, by way of example only, with reference to the accompanying drawings, in which the use of the same reference numbers in different figures indicates similar or identical items or features.

DETAILED DESCRIPTION OF THE INVENTION

Figure 1A:
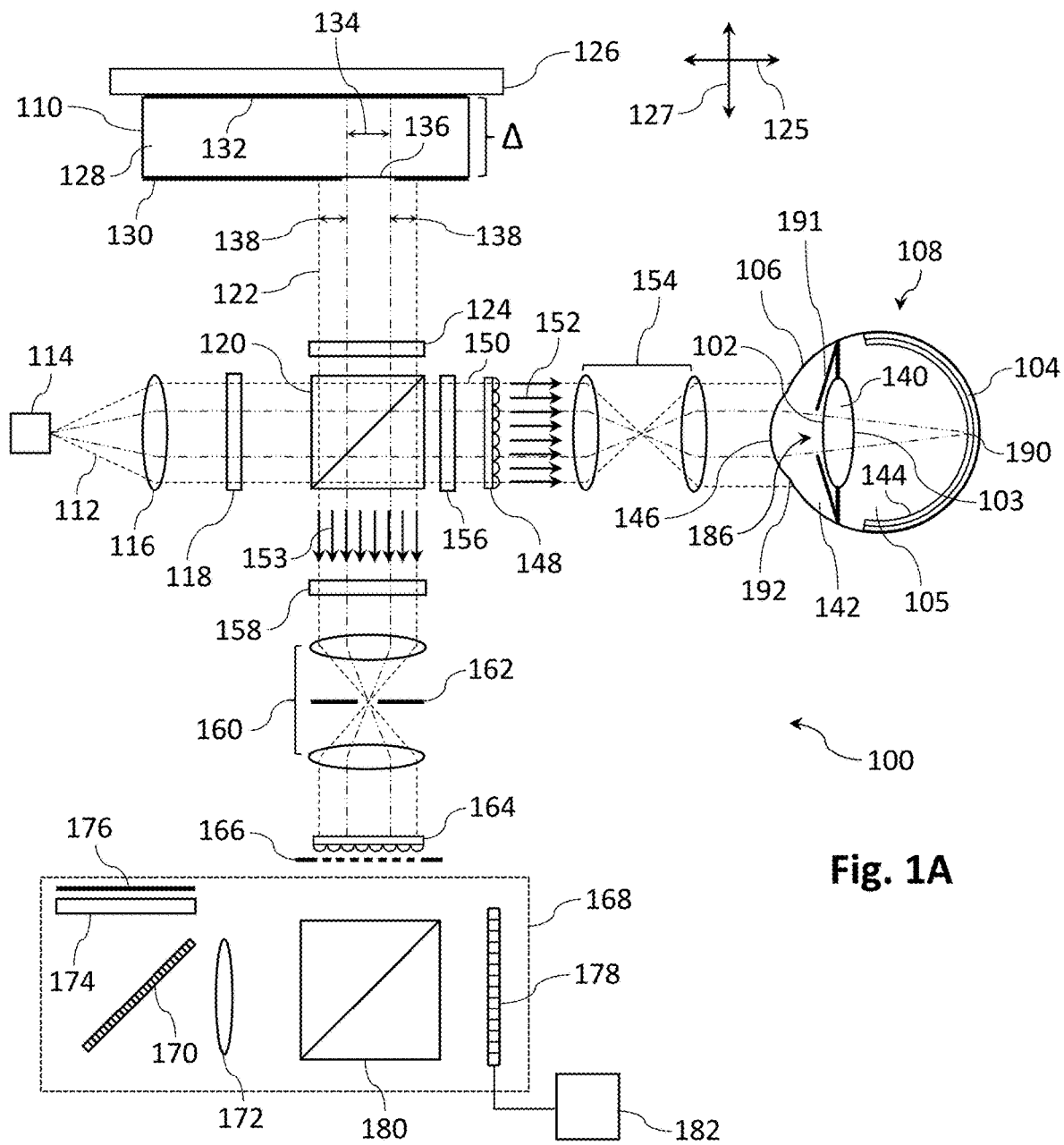
FIG. 1A illustrates in schematic form a spectral domain OCT apparatus for ocular metrology or tomography with registration of intra-ocular interfaces, according to an embodiment of the invention.

A first aspect of the present invention concerns spectral domain OCT apparatus and methods with increased depth of field, in particular having sufficient depth of field for single shot measurement of eye structures and parameters including eye length. FIG. 1A shows in schematic form a spectral domain OCT apparatus 100 according to a first embodiment of the invention, suitable for ocular metrology or tomography with registration of intra-ocular structures, such as the anterior or posterior lens surfaces 102, 103 or the choroid 104, to the anterior sclera 106 of a sample eye 108.

Light 112 from a broadband optical source 114 such as a superluminescent diode with centre wavelength 840 nm and bandwidth of 40 nm is collimated by a collimating element 116 such as a lens or a parabolic mirror, linearly polarised by a polariser 118 and then split by a polarisation beam splitting cube (PBS) 120 into reference and sample beams 122, 150. In preferred embodiments the reference arm includes a multi-length delay element in the form of a compound reflector 110, as well as a quarter wave plate 124 for polarisation transformation so that the light reflected from the compound reflector 110 passes through the PBS 120 and into the detection arm. The reference arm may also include relay elements and dispersion matching components.

In the illustrated embodiment the compound reflector 110 comprises a transparent medium 128 of thickness Δ having a first, apertured reflective surface 130 on its front surface to reflect a first portion 138 of the reference beam 122, and a second reflective surface 132 on its rear surface to reflect a second portion 134 of the reference beam 122 that passes through the aperture 136 of the first reflective surface 130. The reflective surfaces 130 and 132 could for example be metal or thin-film multilayer coatings. In the illustrated 'aperture' position the compound reflector 110 thus functions as a dual length delay element where a first portion 138 of the reference beam 122, in this case an outer portion, receives a delay that is less than that received by a second portion 134, in this case a central portion, by an amount equal to $2 \oplus \Delta \oplus n(\lambda)$ where $n(\lambda)$ is the wavelength-dependent refractive index of the medium 128. In preferred embodiments the medium is chosen to have a dispersion that at least partially compensates for the dispersion of the eye 108, and could for example be water or a low refractive index glass. In this way the delays and hence the coherence properties of the first and second portions 138, 134 of the reference beam 122 can be tailored to match the requirements for coherence with respect to various structures or regions at different depths in the eye 108 being measured, such as the lens 140, retina 144, choroid 104, cornea 146 or anterior sclera 106. In preferred embodiments the compound reflector 110 is mounted on a mechanical stage 126 so that its position can be adjusted both laterally 125 and axially 127. For example the compound reflector 110 may be moved laterally 125 from the 'aperture' position shown in FIG. 1A to a 'plane' position shown in FIG. 1B in which all portions of the reference beam 122 are reflected from the front surface reflector 130 so that there is no differential delay across the reference beam 122. Axial movement 127 of the compound reflector 110 can be used to adjust the path length of the reference arm, i.e. adjust an internal delay in the apparatus 100, e.g. to match different sample positions or to obtain information from structures at different depths in the eye in subsequent tomograms. Alternatively or additionally, the entire apparatus 100 may be moved axially with respect to the eye 108 to adjust the eye to apparatus distance and therefore the path length of the sample arm.

For ocular samples it is convenient for the compound reflector 110 to be in the form of a circular, square or rectangular plate of a transparent material 128, with a centrally located circular aperture 136 in the front reflective surface 130. In certain embodiments the front surface of the compound reflector 110 is anti-reflection coated in the aperture region 136 to minimise front surface reflection of light in the second portion 134 of the reference beam 122. In other embodiments this aperture region 136 is left uncoated, in which case a small fraction of light in the second portion 134, typically 4% for normal incidence at an air/glass interface, will be reflected from the front surface, thereby experiencing the same delay as the light in the first portion 138. This may be useful for example for obtaining interference signals from both the cornea 146 and the retina 144. It yet other embodiments the reflectivity of the aperture region 136 is tailored to select the fractions of reference beam light in the second portion 134 that experience the different delays.

The sample arm comprises a spatial sampling element in the form of a two-dimensional (2-D) lenslet array 148 to generate from the sample beam 150 a 2-D array of sample beamlets 152 which are relayed to the eye 108 via a 4F lens system 154. In certain embodiments the beamlets 152 have identical focal length, while in other embodiments the lenslet array 148 is designed to tailor the focal length of the beamlets depending on their position in the array, e.g. to provide appropriate focusing of various beamlets at different depths in the eye. Advantageously, as shown schematically in FIG. 1C the 2-D array of beamlets 152 can be positioned relative to an eye 108 such that some beamlets 184 enter through the pupil 186 to access the interior of the eye, while other beamlets 188 impinge on one or more anterior surfaces of the eye, preferably including the anterior sclera 106. For the purposes of this specification we define 'an anterior surface' of an eye to be any surface in front of the vitreous humour 105, including without limitation the posterior and anterior lens surfaces 103, 102, and surfaces in the anterior segment 142 including the rear surface of the iris 191, the anterior sclera 106 and the posterior and anterior surfaces of the cornea 146. Light scattered or reflected from various structures of the eye 108 passes back through the relay lens system 154, then is re-focused by the lenslet array 148 and reflected by the PBS 120 into the detection arm following polarisation transformation at the quarter wave plate 156. It will be observed that the path length of the returning sample light will depend on the distance into the eye 108 from which it was scattered or reflected. For example beamlets 188 reflected or scattered from the anterior sclera 106 will have a shorter path length than beamlets 184 that pass through the pupil 186 and are reflected or scattered from the posterior lens surface 103 or the retina 144 for example. In general the number of beamlets 152 relayed onto the eye 108 depends on the design of the 2-D lenslet array 148, and in certain embodiments there may for example be of order 100 or 1000 beamlets in a square or rectangular pattern with a density of, say, 4 to 100 beamlets per square millimetre.

The reflected sample beamlets 153 are combined with the reference beam 122 and the resultant combined beams analysed by a polariser 158 to interfere the light from the sample and reference paths. The resultant interference pattern is relayed by a system of lenses 160, and an optional aperture 162 to remove stray light, for spectral analysis in a spectrometer 168 at a grid of spatial positions determined by a spatial sampling element in the form of a 2-D lenslet array 164, and a corresponding 2-D aperture array 166. Generally, the two lenslet arrays 148, 164 will be aligned so that the returning sample beamlets 153 from the lenslet array 148 are directed into the spectrometer 168. Recalling that the interference between sample and reference beams in an OCT system depends on the relative delay between the sample and reference paths, it can be seen that the different delays imparted to different portions of the reference beam 122 by the compound reflector 110 in the 'aperture' position can compensate for the differing delays of beamlets reflected or scattered from structures or regions at different depths in the eye 108. In one particular embodiment the compound reflector 110 is designed such that the optical path length difference $2 \oplus \Delta \oplus n(\lambda)$ applied to the first and second portions 138, 134 of the reference beam 122 is substantially equal to the optical path length difference between sample beamlets 188, 184 that are reflected or scattered from the anterior sclera 106 on the one hand and the retina 144 on the other hand. In other words the compound reflector 110 may be designed such that the axial separation A between the reflective surfaces 130, 132, and the refractive index $n(\lambda)$ of the medium 128 at the design wavelength $\lambda$, provide a predetermined optical path length difference that substantially compensates for the axial depth of the eye. This enables various axially separated structures or regions of an eye, i.e. structures or regions at significantly different optical depths, to be measured in a single frame of a 2-D sensor array 178. We note that a given compound reflector may for example be optimised for measuring the eyes of adults or children.

The spectrometer 168 is a compact reflective spectrometer able to analyse a plurality of grid points, beams or beamlets simultaneously, or at least within a single frame of a 2-D sensor array 178, as they are dispersed by a wavelength dispersive element in the form of a transmissive grating 170. In the illustrated embodiment the spectrometer is used to analyse a plurality of beams formed by interfering the plurality of returning sample beamlets 153 with the reference beam 122. In this embodiment, because the returning sample beamlets and the reference beam are orthogonally polarised the interference occurs when the polarisation state is analysed by the polariser 158. In other embodiments a polarisation-independent beam combiner can be used to interfere beams in the same polarisation state as is well known in the art. After entering the spectrometer 168 the interfered beams are redirected by a PBS 180 to a lens 172 that collimates the beams for dispersion by the grating 170, followed by double passage through a quarter wave plate 174 via reflection from a mirror 176 to rotate the polarisation state by 90 degrees. In combination the quarter wave plate 174 and the mirror 176 form a polarisation transformation system, which in this case effects a 90 degree rotation. The dispersed spectral components of the reflected light are imaged by the lens 172 onto a 2-D sensor array 178 such as a CMOS camera after passing through a PBS 180. The interferogram detected by the 2-D sensor array is read out in a single frame for subsequent analysis by a computer 182 equipped with suitable computer readable program code. The computer may for example apply well-known Fourier transform techniques to obtain a depth-resolved image, i.e. a three-dimensional (3-D) image of the eye 108. In preferred embodiments the grating 170 is oriented with respect to the grid of spatial positions determined by the 2-D lenslet array 164 and the corresponding 2-D aperture array 166 such that each of the combined beams entering the spectrometer 168 is dispersed onto a separate set of pixels of the 2-D sensor array 178, as described in published US patent application No US 2016/0345820 A1 entitled 'High resolution 3-D spectral domain optical imaging apparatus and method', the contents of which are incorporated herein by reference.

Figure 7A:
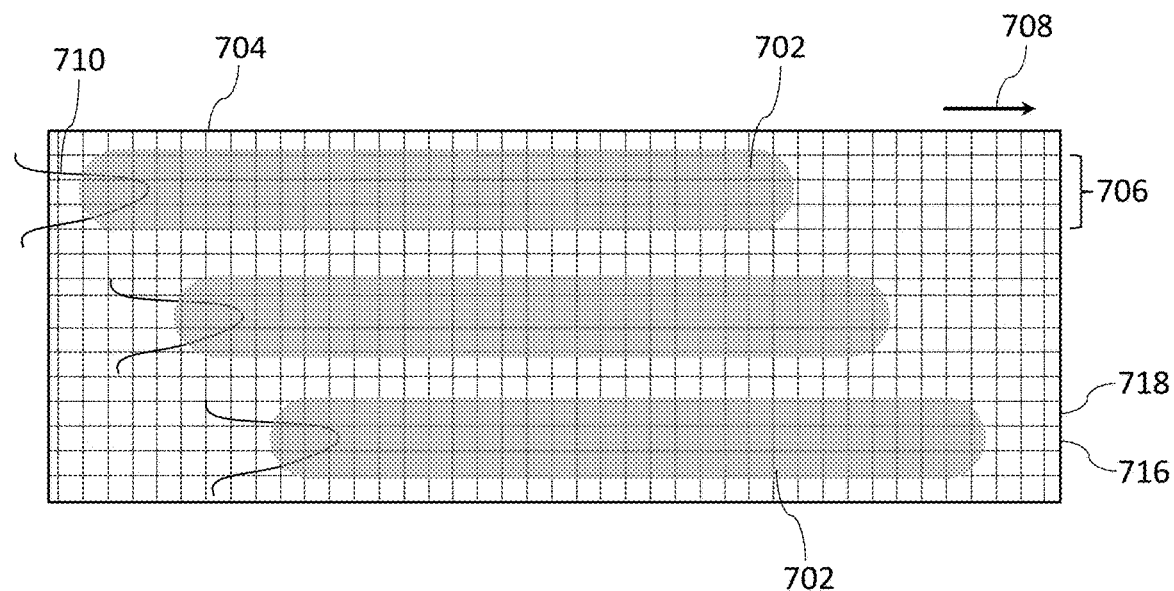
FIG. 7A illustrates in schematic form the projection of three combined beams onto a 2-D sensor array.
Figure 7B:
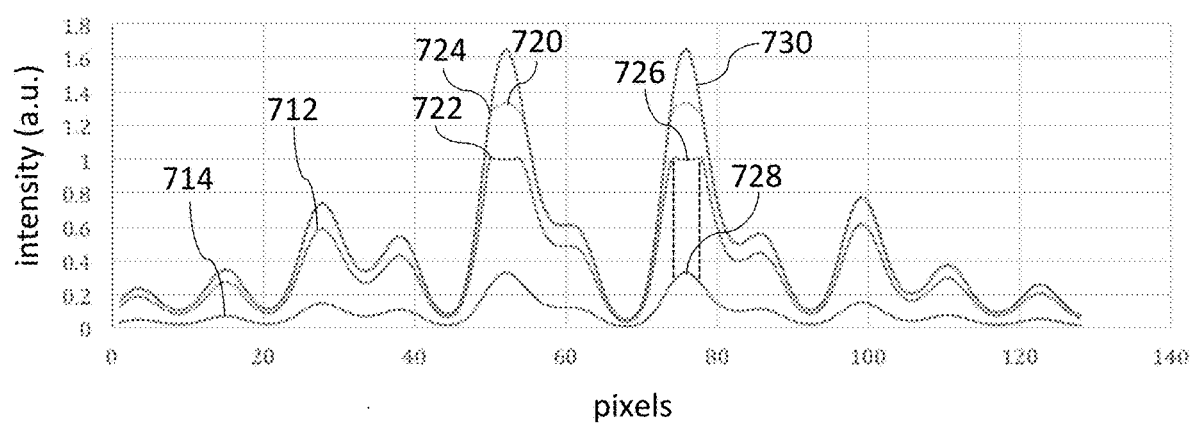
FIG. 7B shows, for one of the beam projections in FIG. 7A, plots of intensity versus pixel number for different rows of pixels of the 2-D sensor array, showing an effect of pixel saturation.

In a preferred embodiment the spectrometer 168 is configured such that each of the combined beams is dispersed onto several parallel sets of pixels of the 2-D sensor array 178. For example FIG. 7A shows in schematic form the projections 702 of three combined beams dispersed onto a portion 704 of a 2-D sensor array. Each projection extends across several rows of pixels 706 in the direction perpendicular to the dispersive axis 708, and will generally have an approximately Gaussian intensity profile 710 in that direction. In the direction parallel to the dispersive axis 708 the projection 702 of a dispersed combined beam will have a varying intensity profile indicative of the interference fringes in that beam. Importantly, the intensity profile of the interference fringes will be replicated across the several rows of pixels 706 so that, in the absence of saturation, reading out any or all of the relevant rows of pixels will yield essentially the same information. However the limited dynamic range of individual pixels, which is determined by the number of photo-electrons that can be stored in each pixel in a single frame, can result in some pixels being saturated. This may occur for example if some beamlets contain relatively intense specular reflections, e.g. from the cornea. To demonstrate this effect FIG. 7B shows, for a representative beam projection 702 in FIG. 7A, plots 712 and 714 of intensity versus pixel number for a central row of pixels 716 and an outer row of pixels 718 respectively. It can be seen that the interference fringes 712 at the central pixel row 716 are clipped at a maximum value, here normalised to 1, whereas the interference fringes 714 at the outer pixel row 718 remain unsaturated. The effect of clipping can also be seen in the plot 720, which shows the sum of the detected intensities from the central and outer pixel rows. Sudden changes in detected intensity, such as the transition 722 to a constant intensity value in plot 712 or the abrupt change of slope 724 in plot 720 will result in the appearance of many higher order frequency components in the spectral domain, which may be manifested as an artefact or streak in the A-scan corresponding to that beamlet. This can be avoided by using the unclipped data from the outer pixel rows. For example the analysis can be confined to using the unclipped pixel data alone, or the pixel data can be processed in such a way as to substitute regions of clipped data 726 with the corresponding unclipped data 728, optionally with some scaling determined from unsaturated regions, to yield a corrected intensity plot 730. These modified analyses generally sacrifice signal to noise to a small extent, but the artefact reduction enables better estimation of a surface boundary in a region of specular reflection.

This artefact reduction technique can also be applied in situations where the dispersive axis 708 is at some angle with respect to the pixel rows in a 2-D sensor array, so long as the beam projections 702 extend across a plurality of pixels in the direction perpendicular to the dispersive axis 708. For each beam projection there will still be at least two sets of pixels extending parallel to the dispersive axis receiving the same interference fringe information but at different intensities.

It should be noted that this artefact reduction technique cannot be applied to OCT apparatus that obtain spatially resolved image data from an illuminated line or area, e.g. as in U.S. Pat. No. 8,534,838, because in these situations the intensity profile from a given sample area is not replicated across several rows or sets of pixels, isolated from the intensity profiles corresponding to other sample areas. This represents an advantage of presenting interference data to a 2-D sensor array in the form of one or more discrete beams, generated for example by the lenslet array 164 as shown in FIG. 1A.

Several variations on the apparatus 100 shown in FIG. 1A are possible. For example the splitting and recombining of the sample and reference beams 150, 122 could be effected with an optical fibre coupler or a non-polarising beam splitter. The apparatus could also be adapted for use with transmissive samples rather than reflective samples such as an eye 108 by using the PBS 120 to split the source light 112 into the sample and reference beams 150, 122, and a separate beam combiner to recombine the beams after the sample beam has passed through the sample. It would also be possible to use a compound reflector 110 with three or more axially spaced-apart reflective surfaces, designed for example for accurate path length matching of light scattered or reflected from the anterior sclera 106, the anterior lens surface 102 and the retina 144. In another variation the 2-D array of sample beamlets 152 could be generated by a spatial sampling element in the form of an aperture mask, a MEMS mirror array or a diffractive optical element rather than a lenslet array 148. Similarly, the lenslet array 164 before the spectrometer 168 could be replaced by an aperture mask, a MEMS mirror array or a diffractive optical element. In yet another variation a spatial sampling element in the form of a 1-D lenslet array or similar could be used to generate a 1-D array of sample beamlets, although in general a 2-D array is preferred for obtaining data across a larger area of a sample in a single frame.

We note that it is not essential for the apparatus to generate an array of sample beamlets 152 for illuminating the eye 108. That is, the various parts of the eye could alternatively be illuminated with the unstructured sample beam 150. However the use of beamlets to illuminate and obtain data from a plurality of discrete points in or on the eye is advantageous not only for the mitigation of pixel saturation as described with reference to FIGS. 7A and 7B, but also for achieving a suitable signal to noise ratio for the weakly scattering structures of the eye, as the sample light is directed to discrete regions of higher intensity and the returning light can be captured from a larger numerical aperture and so provide a stronger signal. As mentioned previously it is also beneficial to be able to tailor the lenslet array 148 or other spatial sampling element to focus different beamlets 152 at different depths within the eye.

Figure 1B:
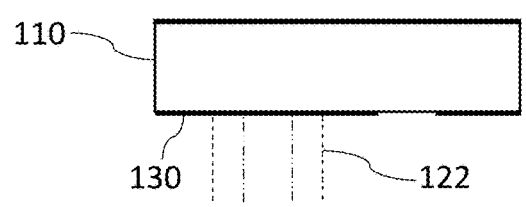
FIG. 1B shows a portion of the reference arm of the FIG. 1A spectral domain OCT apparatus, with a compound mirror in a 'plane' position rather than an 'aperture' position.
Figure 1C:
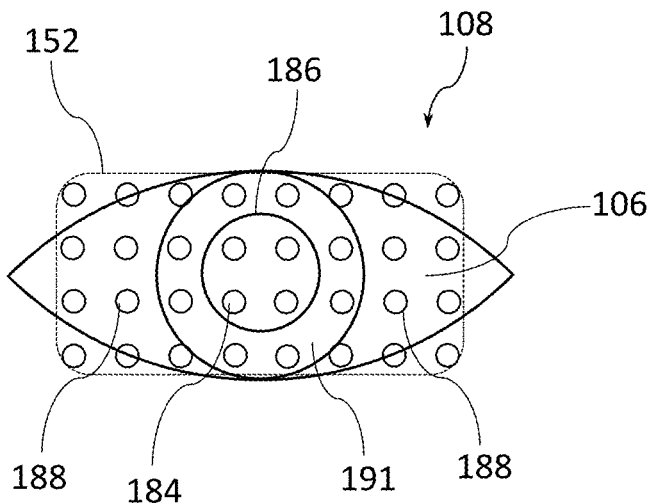
FIG. 1C shows in schematic plan view an advantageous positioning of a 2-D array of sample beamlets on the pupil, iris and anterior sclera of a sample eye, using the FIG. 1A apparatus.
Figure 2A:
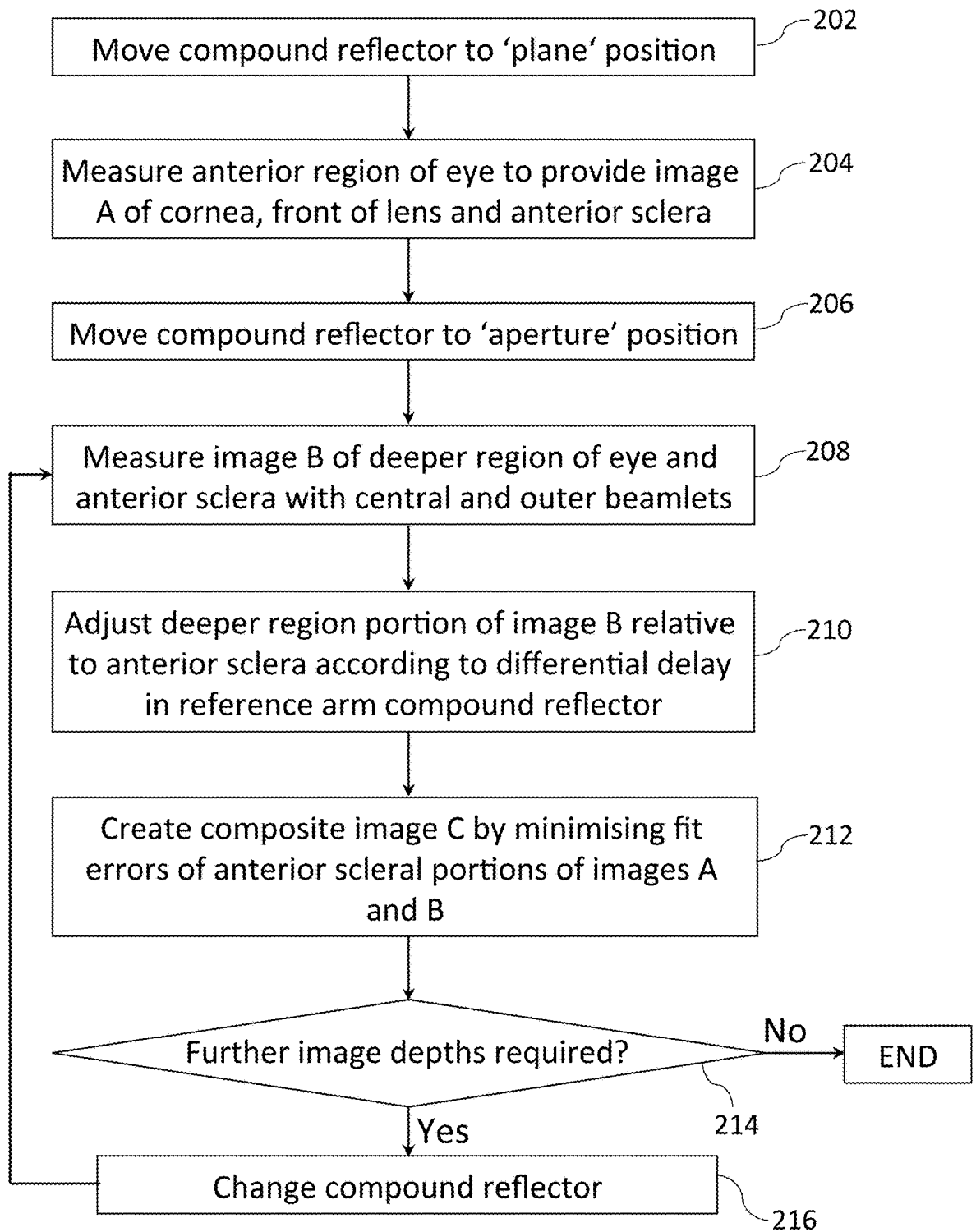
FIG. 2A depicts a flow chart of a method for constructing a composite image of an eye using the FIG. 1A apparatus.

FIG. 2A depicts a flow chart of a method for constructing a composite image or composite tomogram of an eye, using the apparatus 100 shown in FIG. 1A. In step 202 the compound reflector 110 is moved to the 'plane' position, as shown in FIG. 1B, and in step 204 an anterior region of an eye 108 is measured to provide a first image or tomogram, image A. With reference to FIG. 1A and the on-eye positioning of a 2-D array of beamlets 152 shown in FIG. 1C, for this image A at least some of the outer beamlets 188 measure a first region of an anterior surface of the eye, preferably including part of the anterior sclera 106, while at least some of the more central beamlets 184 measure a third region of the eye including the cornea 146 or the anterior lens surface 102 for example. In step 206 the compound reflector 110 is moved to the 'aperture' position, as shown in FIG. 1A. In step 208 a second image or tomogram, image B, is obtained with at least some of the outer beamlets 188 measuring a second region of an anterior surface of the eye, preferably including part of the anterior sclera 106, and at least some of the more central beamlets 184 measuring a fourth, deeper region of the eye, such as the retina 144. The respective anterior surface regions in images A and B should be at least partially overlapping. As shown in FIG. 2C, this means that a first anterior surface region 201-A measured by certain beamlets 188-A in image A should at least partially overlap with a second anterior surface region 201-B measured by certain beamlets 188-B in image B. There may be some overlap of the discrete spots illuminated by individual beamlets when acquiring images A and B, but this is certainly not essential. In step 210 the portion of image B obtained from the fourth, deeper region of the eye is adjusted relative to the portion obtained from the second, anterior region according to the differential delay $2 \oplus \Delta \oplus n(\lambda)$ imposed on the reference beam 122 by the compound reflector 110. Then in step 212 a composite image or composite tomogram, image C, is created by minimising the fit errors of the overlapping anterior portions of the 'A' and 'B' images by allowing for relative translation or rotation between the two images, for example using a localised regression or a nonparametric fit, thereby registering the data from the third and fourth regions of the eye. In step 214 a decision is made as to whether further image depths are required. If so, then another compound reflector with a larger or smaller differential delay is placed in the reference arm in step 216, and the process returns to step 208 for acquisition and computation of additional 'B' and 'C' images. Alternatively, a plurality of 'B' images can be acquired with different compound reflectors before the composite 'C' images are computed. Most if not all of the steps in the flow chart of FIG. 2A will in general be performed by a computer 182 equipped with appropriate computer readable program code, although some of the steps such as moving of the compound reflector 110 may be performed manually.

Figure 2B:
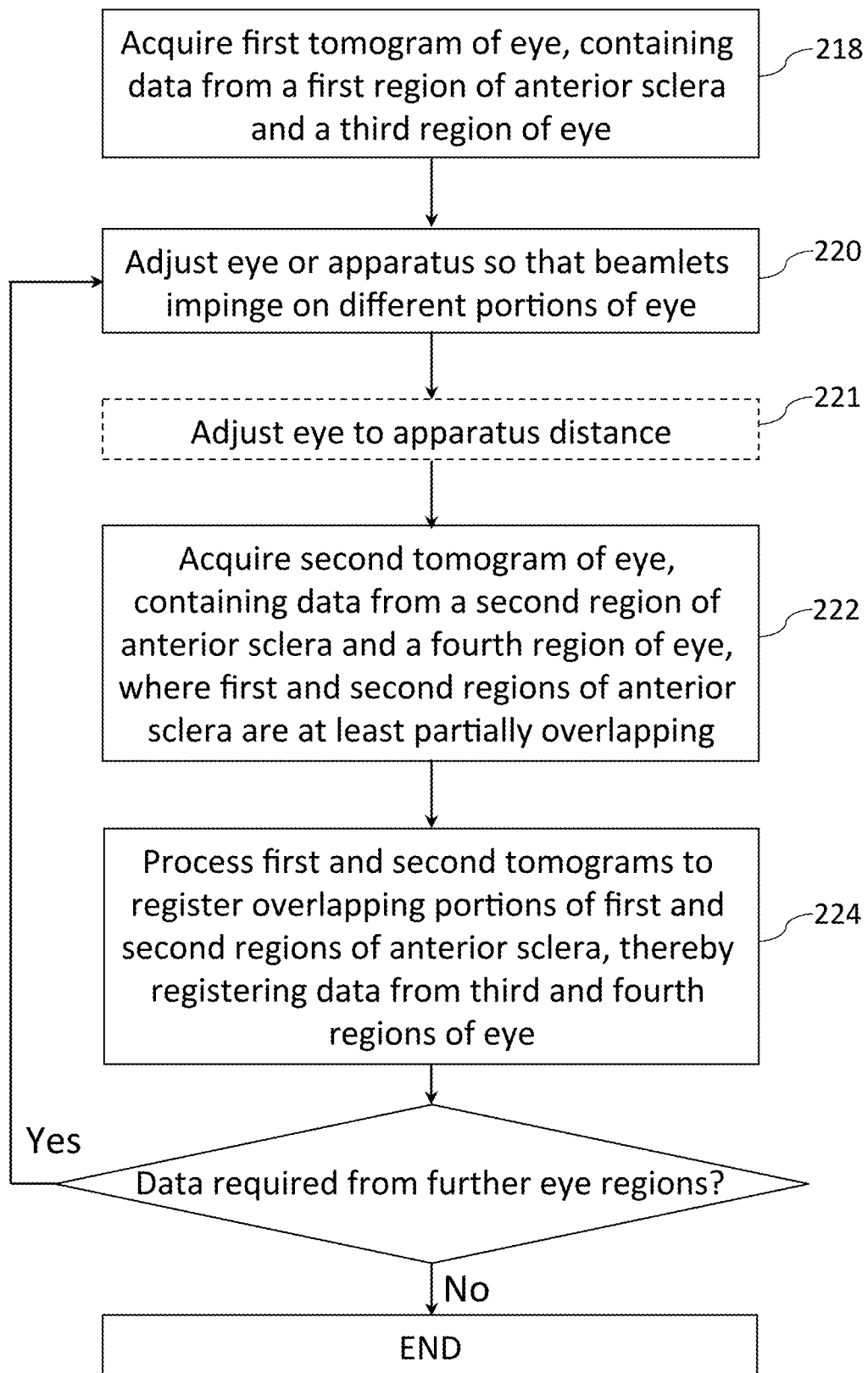
FIG. 2B depicts a flow chart of another method for constructing a composite image of an eye using the FIG. 1A apparatus.
Figure 2C:
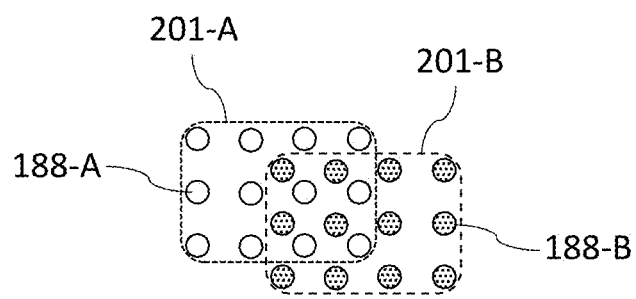
FIG. 2C illustrates in schematic form partially overlapping regions of a sample illuminated by a 2-D array of beamlets in separate measurements.

FIG. 2B depicts a flow chart of another method for constructing a composite image or composite tomogram of an eye using the apparatus 100 of FIG. 1A, with the compound reflector 110 in the 'plane' position as shown in FIG. 1B so that there is no differential delay across the reference beam 122. In step 218 a first optical coherence tomogram or image of an eye 108 is acquired. With reference to FIG. 1A and the on-eye positioning of a 2-D array of beamlets 152 shown in FIG. 1C, this first tomogram or image may contain data from a first region of the anterior sclera 106, measured by at least some of the outer beamlets 188, and data from a third region of the eye including for example a first area of the anterior lens surface 102, measured by at least some of the more central beamlets 184. In step 220 the apparatus 100 or the eye 108 is adjusted, e.g. by moving a fixation target or by rotating the apparatus about the eye, so that the beamlets 152 impinge on different portions of the eye, and the eye to apparatus distance is optionally adjusted in step 221 to control the sample path length. In step 222 a second optical coherence tomogram or image is acquired. This second tomogram or image may contain data from a second region of the anterior sclera 106 that is at least partially overlapping with the first region as explained above with reference to FIG. 2C, and data from a fourth region of the eye including for example a second area of the anterior lens surface 102. Finally in step 224 the first and second tomograms are processed to register the overlapping portions of the first and second regions of the anterior sclera 106, thereby registering the data from the third and fourth regions of the eye. The registration of the overlapping portions of the first and second regions of the anterior sclera 106 may for example comprise a localised regression or nonparametric fit, to compensate for relative translation or rotation between the first and second tomograms. If data from further regions of the eye is required, e.g. from further areas of the anterior lens surface 102, then steps 220 to 224 can be repeated. Alternatively, several tomograms or images of various eye regions can be acquired before they are registered using data from overlapping portions of the anterior sclera. Again, most if not all of the steps in the flow chart of FIG. 2B will in general be performed by a computer 182 equipped with appropriate computer readable program code.

The method depicted in the flow chart of FIG. 2B can also be applied to measure the retina, with the compound reflector 110 in the 'aperture' position so that a first portion 138 of the reference beam 122 has a shorter path length than a second portion 134. With reference to FIG. 1A and the on-eye positioning of a 2-D array of beamlets 152 shown in FIG. 1C, in this case at least some of the more central beamlets 184 measure different regions of the retina 144 in the first and second tomograms, which can be registered by registering the overlapping portions of the anterior sclera measured by at least some of the outer beamlets 188. The differential delay imposed on the reference beam 122 by the compound reflector 110 could also be beneficial for obtaining data from other relatively deep parts of the eye, such as the posterior lens surface 103, or even from the anterior lens surface 102 if the depth of field of the apparatus 100 would ordinarily be insufficient.

Each of the images or tomograms acquired in the methods depicted in FIG. 2A or FIG. 2B should be acquired in a sufficiently short period of time for the effects of eye movement to be negligible, e.g. within 2 milliseconds, more preferably within 1 millisecond. Even more preferably, each of the images or tomograms is acquired within 100 microseconds to reduce fringe fading caused by eye movement. Eye movement that occurs between acquisition of the tomograms is less critical, since this can be compensated for by the registration of the overlapping anterior portions of the respective images or tomograms. In compensating for the effect of eye motion the optical effects of the eye on the beamlets propagating within the eye can be computed straightforwardly, as would be evident to one skilled in the art.

There are a number of advantages in using information from the anterior sclera 106, preferably including the limbus 192, i.e. the interface between the cornea 146 and the sclera, rather than, say, the cornea, for registering the various images or tomograms, e.g. an 'A' image and one or more 'B' images, acquired from an eye 108. For example the anterior sclera is more strongly scattering than the cornea, providing a larger signal. Furthermore the shape of the anterior sclera often provides stronger identifiable geometrical features than that of the cornea, particularly at the limbus 192, which improves the rotational registration of images or tomograms. It will be appreciated that because the cornea 146 has only weak variation in curvature and is substantially rotationally symmetric, it would be more difficult to align images or tomograms rotationally using beamlet data from the cornea alone. For the purposes of this specification the limbus 192 is considered to be part of the anterior sclera 106.

We will now describe some examples of the construction of a composite image or composite tomogram of an eye using the apparatus of FIG. 1A with a (840±30) nm broadband source 114 and a 2-D CMOS camera 178. No differential delay across the reference beam 122 was required, since the depth of field of the apparatus was sufficient for the range of interest in these examples, from the apex of the cornea 146 to the posterior lens surface 103.

Figure 8:
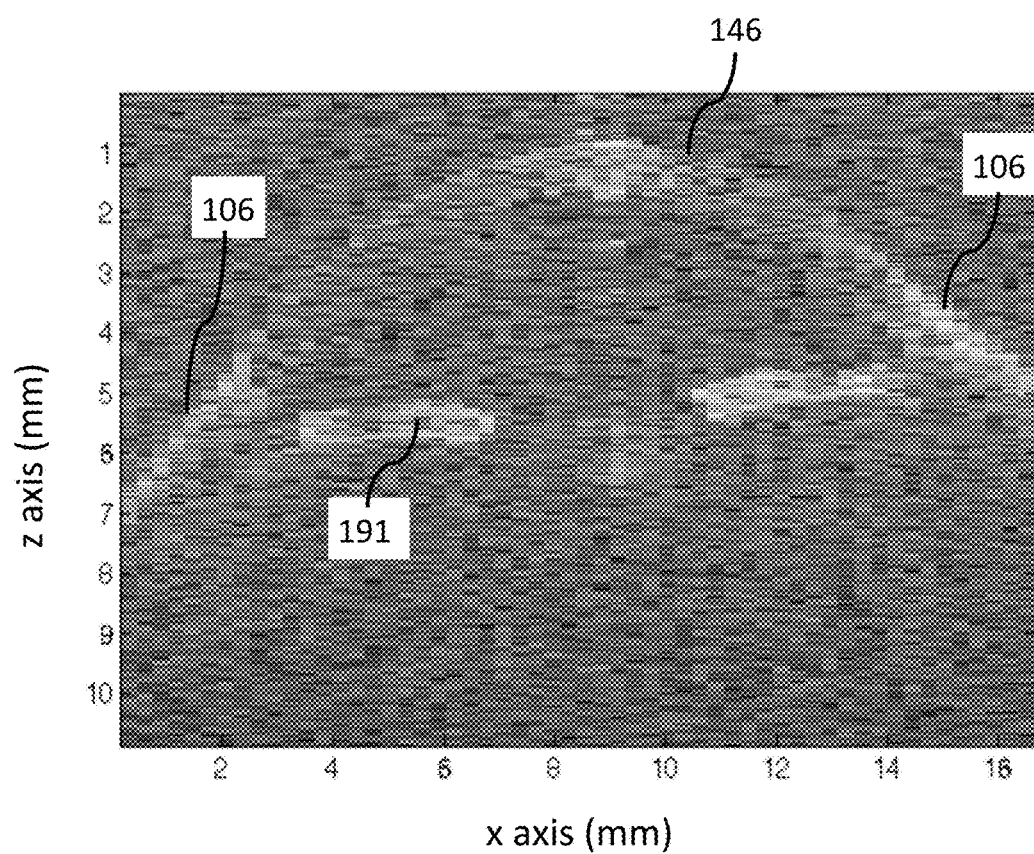
FIG. 8 shows a coarsely sampled 'B-scan' of the anterior segment of a sample eye, consisting of a row of 56 A-scans on a 0.3 mm pitch extracted from one of a raster-scanned set of 144 frames.

FIG. 8 shows a representative coarsely sampled 'B-scan' of the anterior segment of an eye, in which the cornea 146, iris 191 and parts of the anterior sclera 106 can be discerned. This B-scan image consists of a row of 56 A-scans on a 0.3 mm pitch, extracted from a coarsely sampled grid of 18×56 beamlets captured in a single frame of the CMOS camera. In this example a registered volume will be constructed from a total of 144 such frames sampled at a rate of 44 F/s. The grid of beamlets is scanned in a pattern with 25 µm steps, such that after the 144 frames each beamlet has covered an area of 0.3 mm×0.3 mm and the total area covered by all beamlets is 5.4 mm×16.8 mm.

Registration of the 144 frames is achieved by finding appropriate translations and rotations for each frame. For accurate registration of frames we prefer to use a reference surface that provides a relatively strong signal and has regions of significant slope and extent. Considering the poor signal-to-noise ratio (SNR) of an individual frame as is evident in FIG. 8, it can be seen that anterior scleral regions 106 from about 0 to 2.5 mm and 14 to 16.5 mm along the x-axis have a relatively high SNR and slope that can be exploited for registration purposes. The final surface metrology is obtained from the registered volume image.

Figure 9A:
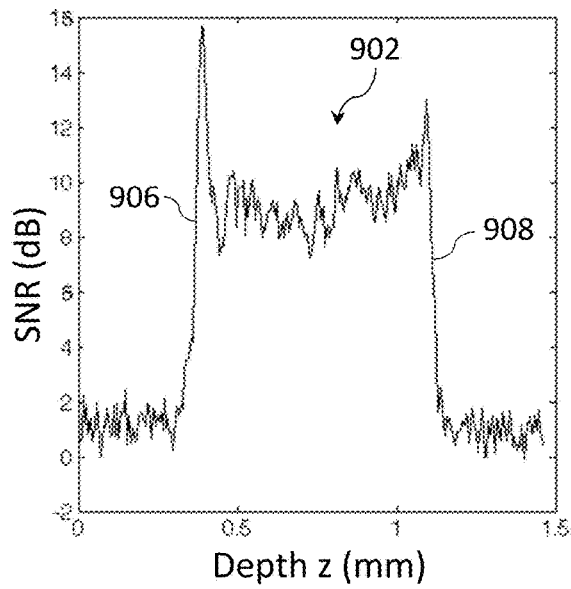
FIGS. 9A and 9B respectively show typical A-scan profiles of the cornea and anterior sclera of an eye.
Figure 9C:
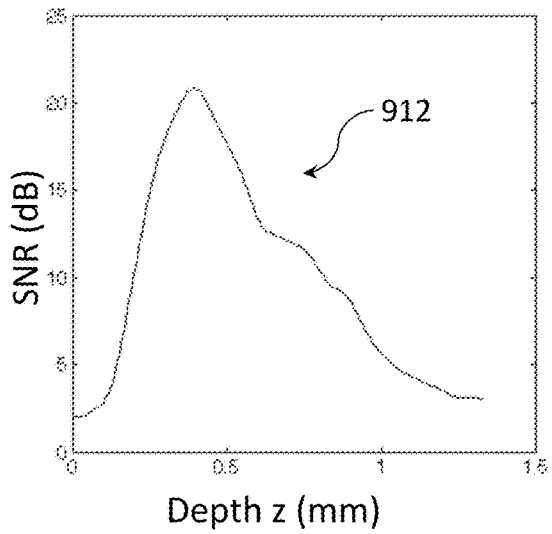
FIG. 9C shows a filter template derived from a number of A-scans of the anterior sclera of an eye.
Figure 9B:
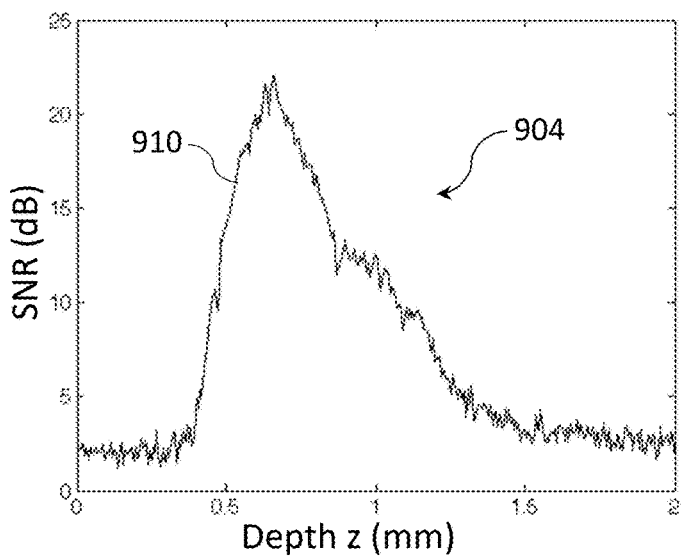
Figure 10:
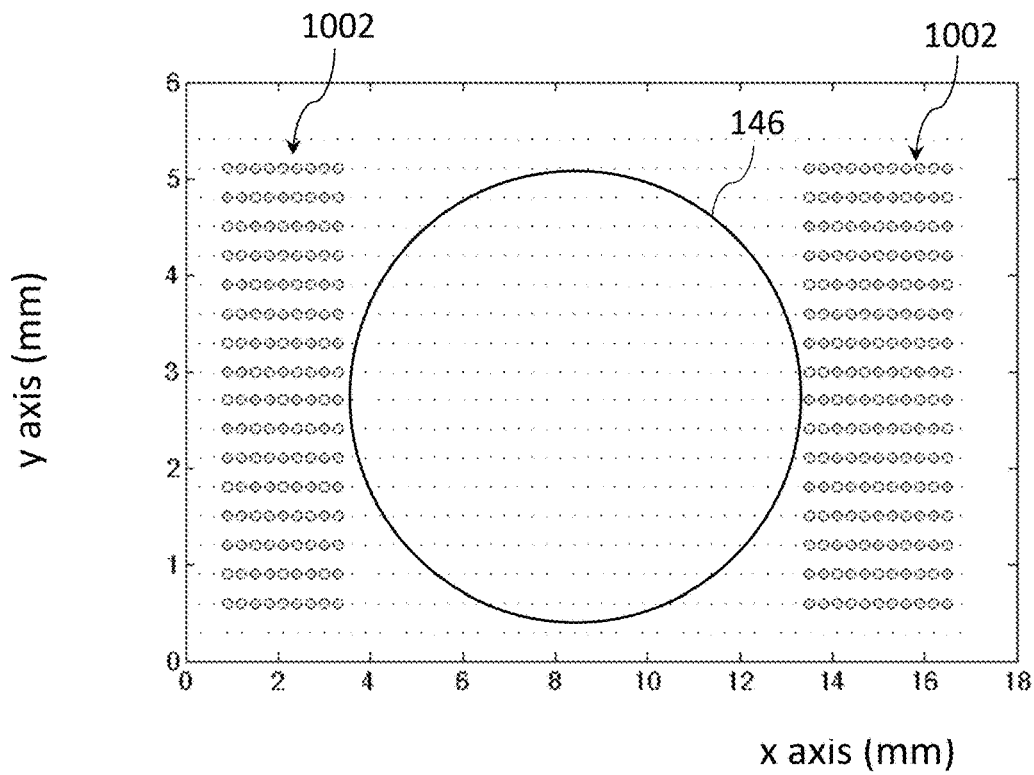
FIG. 10 depicts in schematic form the grid positions of a plurality of A-scans on the anterior sclera of an eye, on either side of the cornea.

It should be noted that the 'surface' used for registration purposes may not necessarily correspond to an actual interface of or in the eye, depending on the interaction between the sample light and the interface in question. By way of example, FIG. 9A shows a typical A-scan profile 902 of the cornea, at a distance of 0.6 mm from the apex, obtained from aligning and averaging A-scans over multiple frames, while FIG. 9B shows a corresponding A-scan profile 904 obtained from the anterior sclera. From these profiles, both of which were obtained using (840±30) nm light, it is clear that although a traditional edge filter may be applicable for detecting either of the sharply defined transitions 906, 908 that correspond to the anterior and posterior corneal surfaces, it would be less well suited for detecting the less clearly defined edge 910 of the scleral A-scan profile 904. It will be appreciated then that the term 'surface' should be interpreted as a depth region proximate to a physical interface. For the specific example of the scleral A-scan profile 904 shown in FIG. 9B, this depth region is approximately ±0.2 mm, but could be larger, for example up to ±1 mm around a physical interface. Instead of using an edge filter for determining the scleral surface, it is preferable to use a filter more closely matched to the shape of a typical scleral A-scan profile, such as the filter template 912 shown in FIG. 9C obtained from averaging a number of scleral A-scans. This filter template 912 is applied to the A-scans corresponding to the beamlets in the scleral region, the grid positions 1002 of which are shown schematically on either side of the cornea 146 in FIG. 10. The surface height for each A-scan is determined from the peak of the filtered signal. We note that in this instance the scleral surface used for registration is not simply an offset of the air/tear film interface, but is dependent on the volume profile of the surface.

An approximate initial reference surface can be obtained from a single frame, and the small scanning range can be exploited to linearise the relationship between change in the surface heights and the translation and rotation vectors. The solutions $\Delta x$, $\Delta y$, $\Delta z$, $\Delta \theta_x$, $\Delta \theta_y$, and $\Delta \theta_z$ can then be found from an efficient least squares approach in which the inputs are the gradient of the reference surface and the surface height of each frame, the height and gradient being evaluated for all scleral A-scans. The relatively low computational cost of this linearised approach enables a second iteration if greater accuracy is required, wherein the output from the first iteration is used as the reference registration surface for the second. In addition, the results of the first stage of registration may be used to provide an axial window so as to minimise the chance of outliers being selected for the second stage of surface detection. The registration computation typically yields a 'volume-averaged' dataset where the sparse volume data corresponding to the measured parameter is binned into a voxel, or distributed into a number of voxels, and the resultant voxel is given values that are the average or weighted average of the contributions to each bin.

Figure 11:
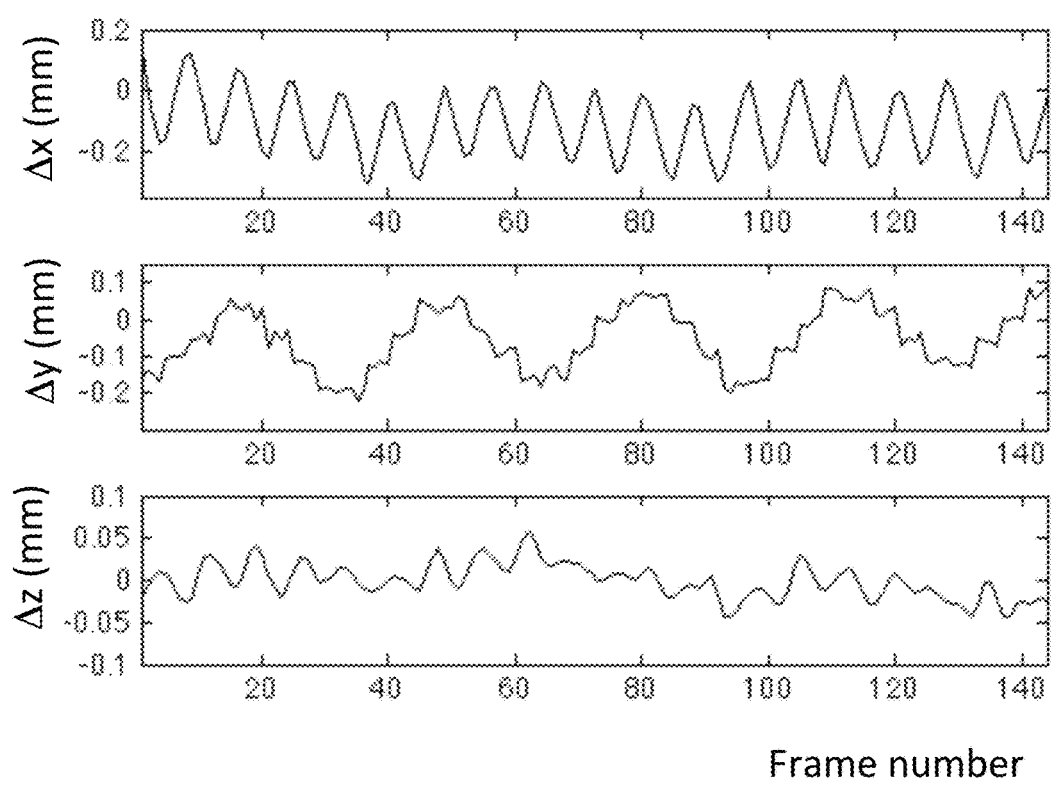
FIG. 11 illustrates the translation vectors used for registering the data acquired from a sample eye in a raster-scanned set of 144 frames.

For the purposes of this example we have restricted registration to translation only, using data from the anterior sclera. The resulting translation vectors are illustrated in FIG. 11, with the periodic pattern of amplitude ~0.3 mm in the x and y axes reflecting the combination of the scan pattern with eye movement during the scan. In general we find up to 1 mm/s of subject movement, and in the example shown the axial movement as shown in the Δz plot is of the order of 0.1 mm over the ~3 s needed to capture 144 frames at 44 F/s.

Figure 12:
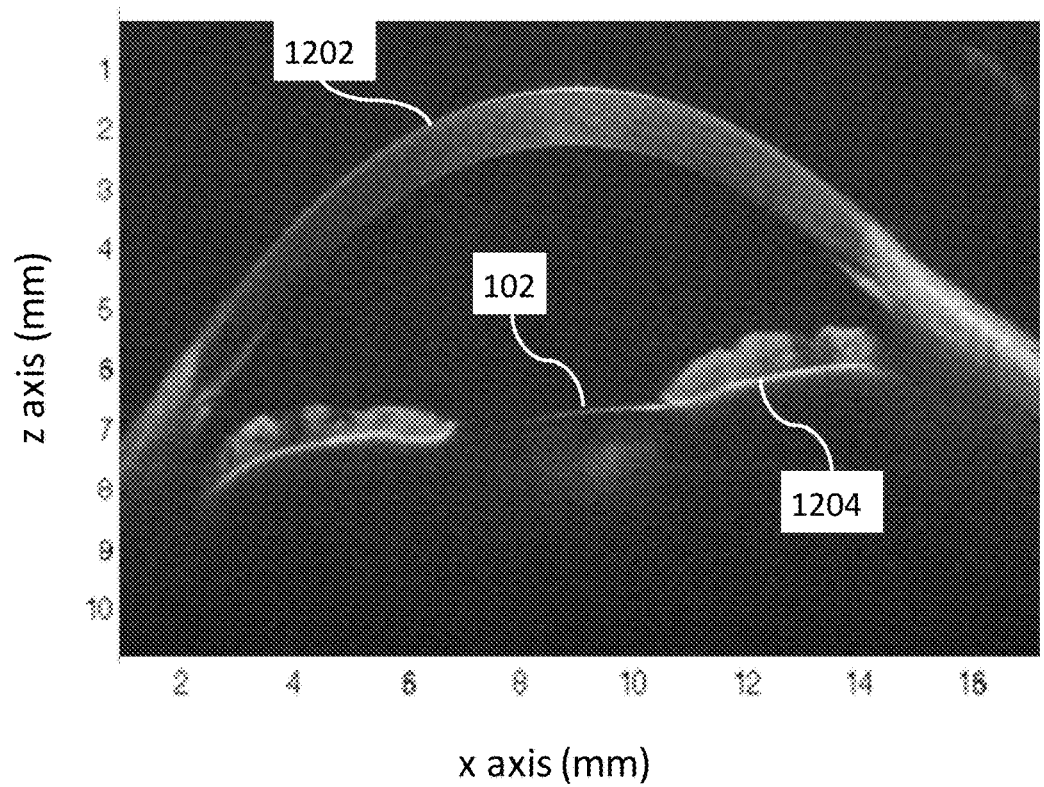
FIG. 12 shows a B-scan of the sample eye of FIG. 8 extracted from a volume-averaged data set obtained from the 144 frames using the translation vectors illustrated in FIG. 11.

FIG. 12 shows a B-scan of the sample eye extracted from a volume-averaged dataset obtained from the 144 registered frames. This image shows several ocular structures with excellent clarity compared to the individual frames, of which FIG. 8 is representative, including the air-tear film interface 1202, the posterior iris surface 1204 and the anterior lens surface 102. With the use of an appropriate filter for identifying it, the air-tear film interface 1202 can be identified and corneal curvature data obtained with good agreement with conventional techniques.

Figure 14:
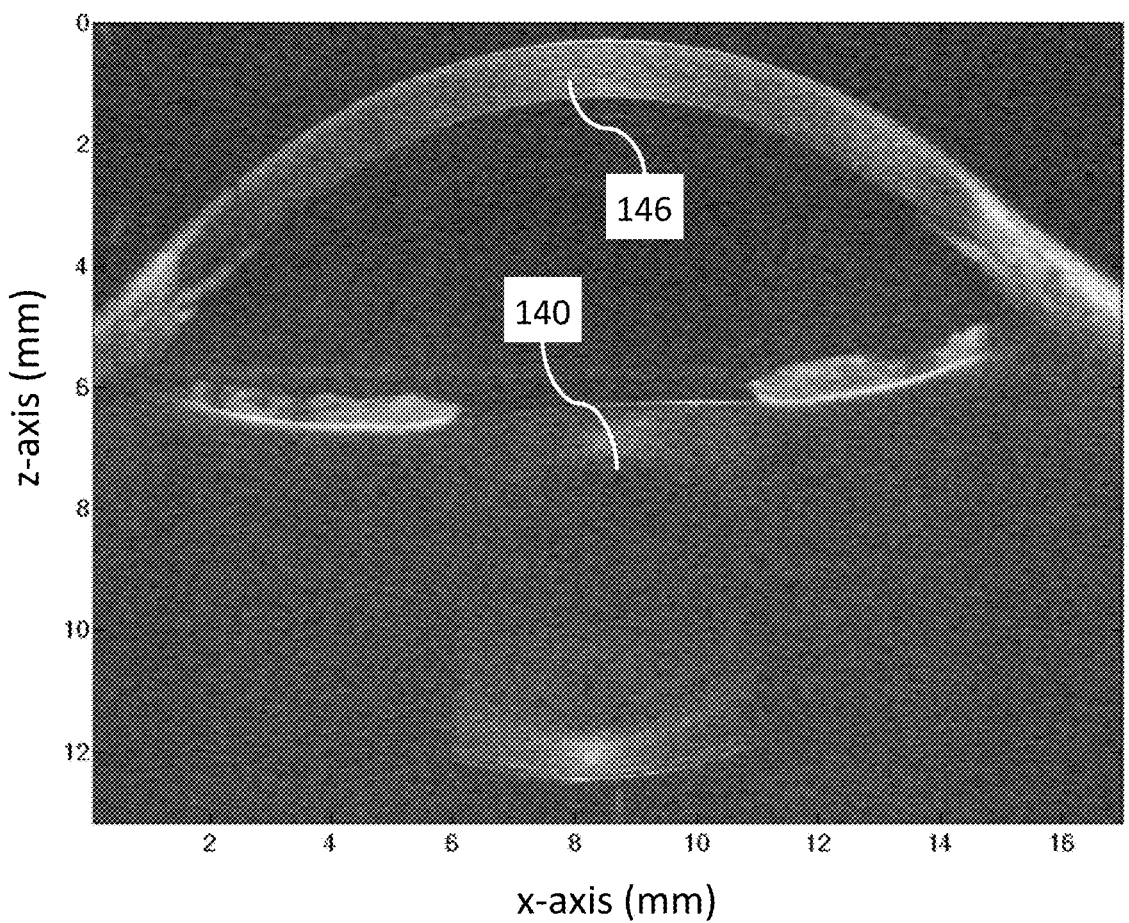
FIG. 14 shows another B-scan of the sample eye of FIG. 13A, this time obtained by co-registering two separate volume-averaged data sets acquired with the instrument position varied to focus at different depths.
Figure 13A:
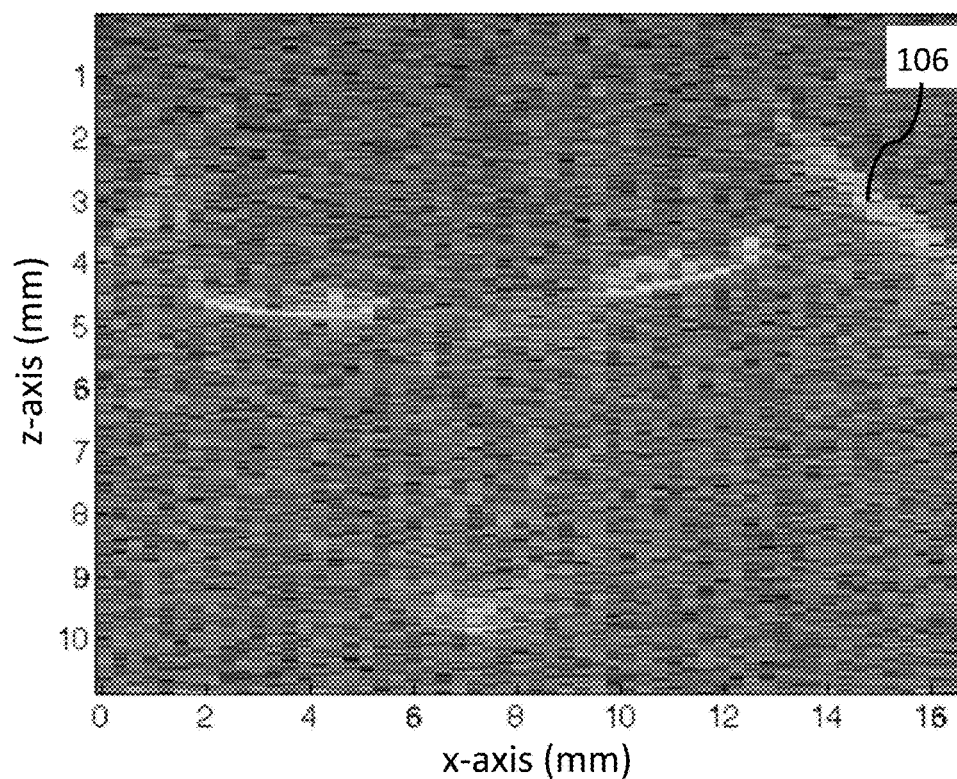
FIG. 13A shows a coarsely sampled 'B-scan' of the lens region of a sample eye, consisting of a row of 56 A-scans on a 0.3 mm pitch extracted from one of a raster-scanned set of 144 frames.
Figure 13B:
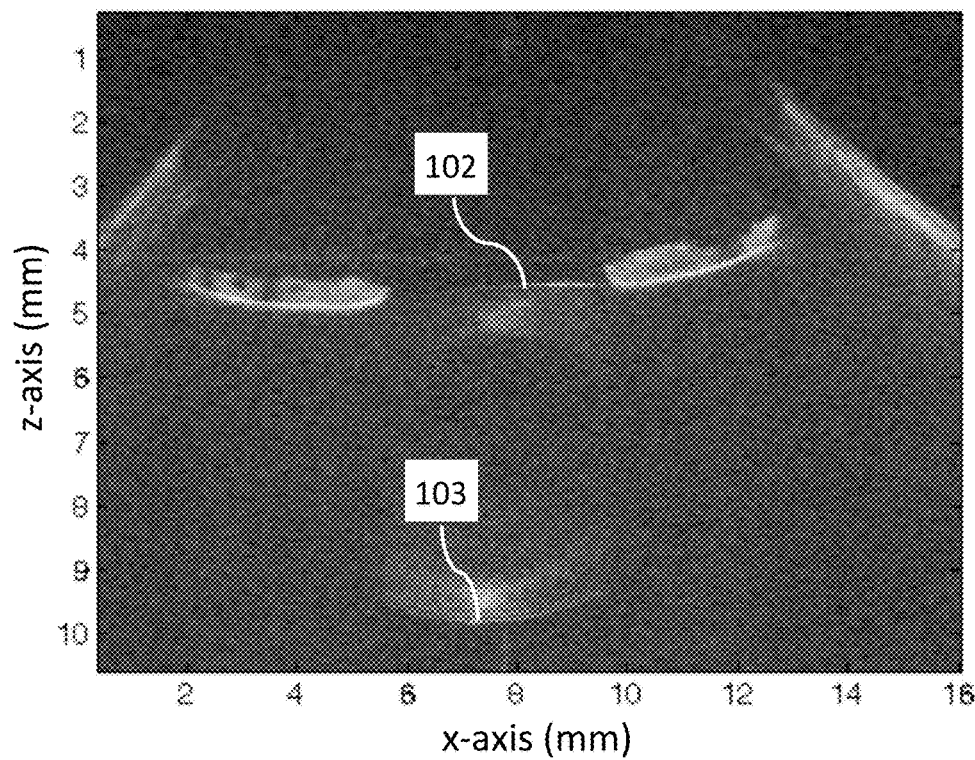
FIG. 13B shows a B-scan of the sample eye of FIG. 13A extracted from a volume-averaged data set obtained from the 144 registered frames, showing the anterior and posterior lens surfaces.

In a second example, FIG. 13A shows a coarsely sampled B-scan of the lens as extracted from a single frame of 18×56 A-scans on a 0.3 mm pitch, similar to FIG. 8. As in the previous example the anterior scleral region 106 is used for registration of a total of 144 frames. A B-scan extracted from the volume-averaged registered frames is presented in FIG. 13B, clearly showing the anterior and posterior lens surfaces 102, 103. In calculating this image the anterior scleral reference provided registration information. FIG. 14 is a volume-averaged B-scan showing both the cornea 146 and lens 140 obtained by additionally registering a second volume-averaged measurement of the corneal region, acquired with the instrument position varied relative to the eye so as to focus at a different depth. In this case registration of the volume-averaged corneal and lens images is based upon the common anterior scleral regions of the two datasets. We note that as an alternative, joint registration of the cornea and lens may be achieved by registering individual corneal and lens frames with respect to a common scleral reference surface prior to volume averaging. Importantly, co-registration of the scleral region enables a large depth range composite image to be obtained while maintaining the measurement accuracy, despite significant patient movement between acquisitions. We note that the volume-averaged B-scans shown in FIGS. 12, 13B and 14 are raw images, i.e. prior to calibration and refraction correction using techniques known in the art.

Figure 3:
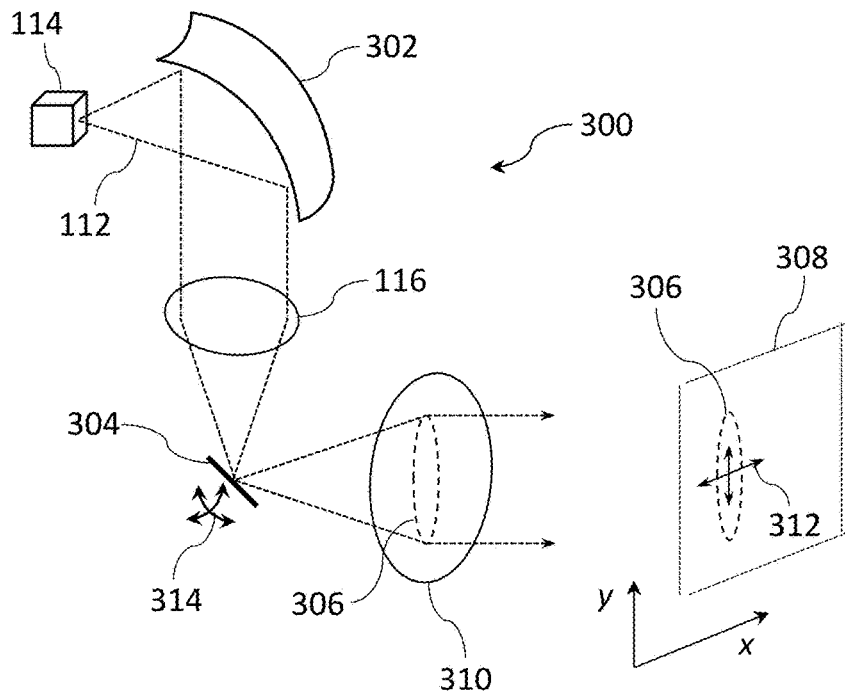
FIG. 3 shows in schematic oblique view an alternative illumination system for the FIG. 1A apparatus.

In the OCT apparatus 100 shown in FIG. 1A, information from all parts of the eye 108 accessed by the array of beamlets 152 is collected simultaneously by the 2-D sensor array 178. However this can result in the outer beamlets having less intensity than the more central beamlets because of the approximately Gaussian or Lambertian intensity profile of many light sources. FIG. 3 shows in schematic oblique view an alternative illumination system 300 for creating a more uniform illumination over an extended area than the basic combination of a superluminescent diode (SLD) 114 and lens 116 shown in FIG. 1A. Light 112 from an SLD 114 is focused by a parabolic mirror 302 and a lens 116 onto a MEMS mirror 304 which is able to scan during a single acquisition frame of a 2-D sensor array used to acquire an OCT image or tomogram. The beam 306 produced by the SLD 114, parabolic mirror 302 and lens 116, which is typically highly elliptical, can be manipulated 312 into an effective beam of a desired shape 308, e.g. to match the form of a 2-D lenslet array, by high speed angular dithering 314 of the MEMS mirror 304 in one dimension (x-axis or y-axis) or two dimensions (x- and y-axes) before collimation at a second lens 310. Operation of the OCT apparatus proceeds as described previously with reference to FIG. 1A, including spatial sampling of the sample light with a 2-D lenslet array 148 or similar, except that groups of beamlets containing information from different lateral sections of the eye 108 impinge sequentially on the 2-D sensor array 178. Provided the scanning 314 of the MEMS mirror 304 is fast compared to eye motion, the fringe visibility of the interference pattern or the stability of snapshot single frame images acquired by the 2-D sensor array 178 will not be affected by eye motion. That is, individual images or tomograms can still be acquired in a sufficiently short period of time for the effects of eye movement to be negligible.

Although from a metrology perspective a 'snapshot' technique, equivalent to a global shutter, is preferred to capture a whole image or tomogram simultaneously, it is not essential. The use of a scanning mirror 304 is analogous to a rolling shutter in a camera, and provided certain criteria are maintained this can improve the signal to noise of an image or tomogram as well as the uniformity of the signal to noise over the field of view. To achieve this improvement while staying within certain predetermined limits we can define a time t that represents the time limit for ensuring that the phase stability of an interferogram is maintained. Typically a value of around 100 microseconds for t is suitable for a patient fixating on a target, corresponding to axial movements of less than a quarter wavelength (typically around 0.2 μm), and is the exposure time limit for any individual beamlet as the MEMS mirror 304 scans the source light 112 over the associated lenslet array (not shown in FIG. 3). A second time period T can be defined as the frame exposure time, which for ocular metrology can typically be around a millisecond without significantly degrading the quality of the metrology. It is then preferred to match the width x of the scanning beam 306 to the frame width X such that x/X is approximately equivalent to t/T to enhance the signal to noise ratio without degrading the measurement accuracy beyond a predetermined level. Pairs of anamorphic prisms or cylindrical lenses can be included in the illumination system 300 if required, for independent control of the width x and height y of the beam 306 produced by the SLD 114, parabolic mirror 302 and lens 116.

Figure 6:
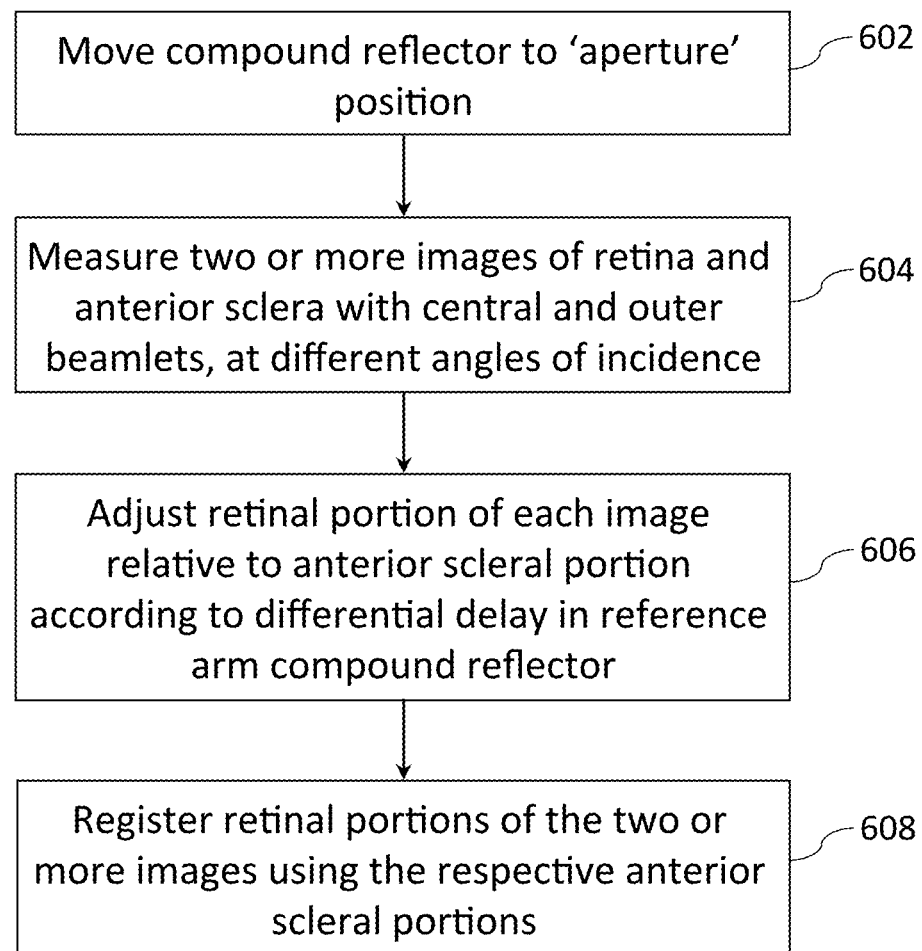
FIG. 6 depicts a flow chart of a method for measuring an eye at different angles of incidence using the apparatus shown in FIG. 1A.

Returning to FIG. 1A, it will be appreciated that when the cornea 146 of a normal unaccommodated eye 108 is illuminated by an array of parallel beamlets 152 as shown, light from all of the beamlets that enter the pupil 186 will be received at a single area 190 of the retina 144 with diameter corresponding to twice the numerical aperture of the beamlets multiplied by the focal length of the eye. These beamlets interfere with each other, thus creating a structured illumination of the retina, but it is difficult to extract much laterally resolved information. Consequently the retinal portion of an image obtained is largely just an average of the structure in that area 190. This measurement can be repeated for different angles of incidence, allowing the eye's axial length to be measured accurately across an extended range of the retina by having the patient track a movable fixation target, or by rotating the apparatus 100 relative to the eye 108. The overall process, which provides information on total eye shape, is depicted in the flow chart shown in FIG. 6. In step 602 the compound reflector 110 is moved to the 'aperture' position, and in step 604 two or more images or tomograms of an eye 108 are measured at different angles of incidence, e.g. by moving a fixation target or rotating the apparatus 100 relative to the eye. With reference to FIGS. 1A and 1C, each image or tomogram contains data from an anterior surface of the eye, preferably including the anterior sclera 106, provided by at least some of the outer beamlets 188, and data from a localised area 190 of the retina 144 provided by at least some of the more central beamlets 184. The respective anterior surface data should be at least partially overlapping, as explained above with reference to FIG. 2C. In step 606 the retinal portion of each image or tomogram is adjusted relative to the anterior surface portion according to the differential delay $2 \oplus \Delta n(\lambda)$ imposed on the reference beam 122 by the compound reflector 110. Finally in step 608 the retinal portions of the two or more images or tomograms are registered using the overlapping portions of the respective anterior scleral data. Most if not all of the steps in the flow chart of FIG. 6 will in general be performed by a computer 182 equipped with appropriate computer readable program code. The process shown in FIG. 6 can provide useful metrology at distinct locations, e.g. to provide information on total eye shape, although it can be time consuming in a clinical setting.

It will be shown however that by inserting an additional lens before the eye, or by appropriate modification of the sample arm relay optics, the imaging optical system shown in FIG. 1A can be modified to deliver an array of angularly dispersed beamlets that will be focused onto the retina over a grid of discrete points that can be measured simultaneously, or at least in a single frame of a sensor array. This can be used to image extended areas of the retina by dithering the position of the beamlet array, e.g. by using a MEMS mirror in the relay optics of the sample arm. To go further and create an accurate metrology of eye shape as can be important in applications such as diagnosis and monitoring of myopia progression, it is necessary to go beyond imaging to determine axial length accurately at different positions on the retina using illuminating beams at different angles. To do so, this measurement needs to be referenced to the position of the measuring instrument relative to the eye, as described further below. It also requires knowledge of the shape of the cornea and subsequent layers of the eye, which can be measured using the apparatus and techniques described above with reference to FIG. 1A.

Figure 4:
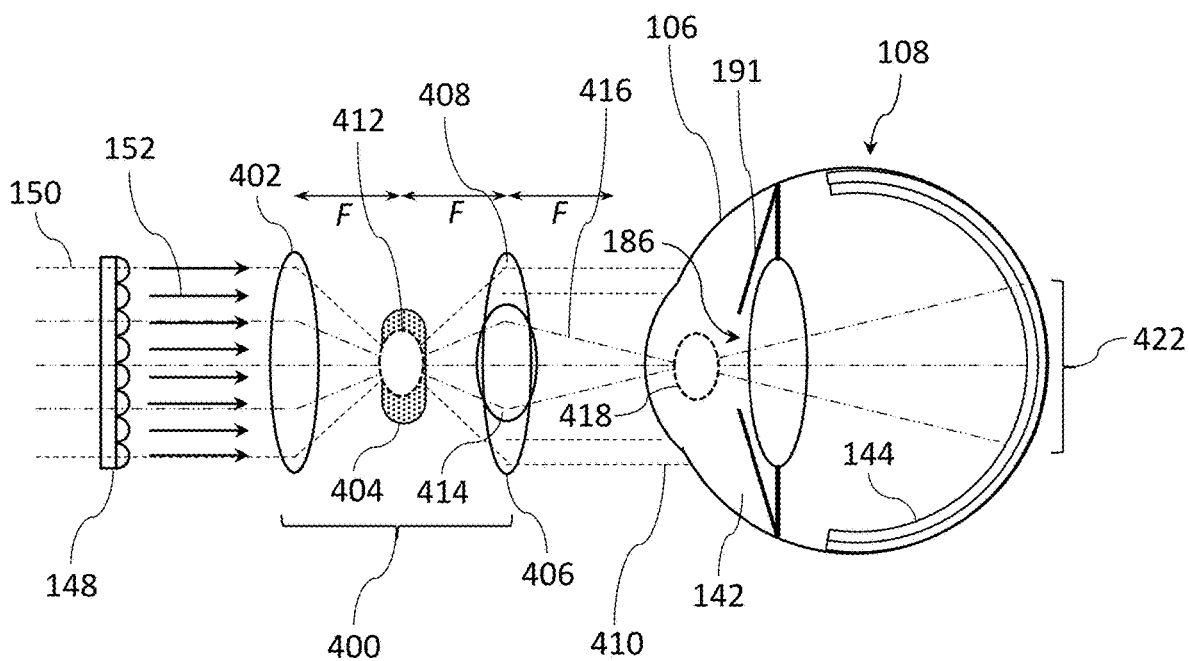
FIG. 4 illustrates in schematic form the sample arm optics of an OCT apparatus, according to an embodiment of the invention.

Accordingly, FIG. 4 shows in schematic form a modification of the sample arm relay optics of the apparatus shown in FIG. 1A, to provide a spectral domain OCT apparatus according to a second embodiment of the invention. As in FIG. 1A, a sample beam 150 emerging from a PBS 120 and a quarter wave plate 156 (not shown in FIG. 4) is transmitted though a spatial sampling element in the form of a 2-D lenslet array 148 to form an array of parallel beamlets 152. In certain embodiments the beamlets form a uniform array, while in other embodiments they may have different waist sizes depending on their positions within the array, determined by the properties of the lenslets in the lenslet array 148, in particular focal length. The array of beamlets 152 then encounters a relay system 400 that is significantly different from the 4F lens system 154 of FIG. 1A. In this second embodiment the relay system 400 comprises a conventional lens 402 with focal length F, a MEMS mirror 404 for dithering the on-eye position of the set 412 of angularly dispersed beamlets, and a compound lens 406 having two parts 408, 414 with distinct focal lengths for acting on different subsets of beamlets 410, 416. For simplicity of illustration the MEMS mirror 404 is shown as being transmissive rather than reflective. In certain embodiments the compound lens 406 is a unitary structure with distinct parts 408, 414 as shown, manufactured for example by replicated diamond turning. Alternatively it could comprise two or more lenses located adjacent to each other to provide a multi-element lens designed to reduce aberrations of both the central beamlets 416 and the peripheral beamlets 410. In preferred embodiments the apparatus includes a mechanism for interchanging the compound lens 406, such as a lens mounting bracket or a lens wheel. Replacement compound lenses could for example have different pairings of focal lengths, different relative sizes of the distinct parts 408, 414, or more than two distinct parts. In yet another variation the compound lens could be replaced by a conventional lens, preferably matched to the lens 402 to provide a 4F relay system 154 as shown in the apparatus of FIG. 1A. This offers a low-cost means for providing an instrument that is additionally capable of operating in that configuration, optimised for measuring anterior eye structures.

An outer part 408 of the compound lens 406 relays a peripheral subset 410 of the angularly dispersed set 412 of beamlets onto the anterior segment 142 of the eye 108, preferably including part of the anterior sclera 106. In this particular example the outer part 408 of the compound lens has focal length F, equal to that of the first lens 402, to provide a non-magnifying telecentric relay system with the peripheral beamlets 410 propagating in parallel. Alternative embodiments with non-unitary magnification or non-telecentric imaging, e.g. by inclusion of an optical wedge, can provide a divergent or convergent set of peripheral beamlets. Either way, the relayed peripheral beamlets enable the acquisition of information from a grid of points in or on the anterior segment 142, preferably including part of the anterior sclera 106.

The focal length of the inner part 414 of the compound lens 406, in this example F/2, is chosen to re-image a central subset 416 of the angularly dispersed beamlets 412 onto the retina 144. A range of focal lengths for the inner part 414 of the compound lens will achieve this, with the choice of F/2 providing an inverted image 418 of the central beamlets 416 from the MEMS dithering mirror 404 which is positioned at a distance F from the compound lens 406. This inverted image 418 could lie either within or external to the anterior segment 142, so long as a significant proportion of the central beamlets 416 are transmitted through the pupil 186 and relayed to the retina 144. The optical power of the eye 108 transforms the angularly dispersed, relatively large area beamlets 416 to a spatially dispersed array 422 of more focused beamlets on the retina. The MEMS mirror 404 simultaneously dithers the positions of both the central beamlet array 422 on the retina 144 and the peripheral beamlets 410 on the front of the eye 108, with the peripheral beamlets providing a reference for registering the retinal imaging measurements of the central beamlets as explained previously.

It will be appreciated that an OCT apparatus modified in the fashion shown in FIG. 4 is advantageous for laterally resolved imaging of an extended area of the retina 144. Furthermore it can provide ocular measurements useful for tracking the progression of myopia in patients and for monitoring the efficacy of treatments used to influence the progression. Advantageously, the modified sample arm relay optics 400 enables near-simultaneous registration of the whole 2-D array of beamlets 152. One subset of beamlets 410, which may for example be parallel or convergent, impinges on the anterior segment 142 of the eye, preferably including the anterior sclera 106, to provide registration for data obtained with a second, angularly dispersed subset of beamlets 416 that pass through the pupil 186 and are mapped using the optical power of the eye across a region 422 of the retina 144. Importantly, this configuration can also provide small diameter beamlets incident on both the corneal or scleral region on the one hand, and the retina on the other. For example the relay optics can be designed such that for both the scleral and retinal areas the beamlets are less than 50 µm in diameter. Smaller beamlets at the retina will provide higher resolution imaging of the retina, but with reduced depth of focus. In general a compromise between these two factors is provided by employing a beamlet diameter of between 5 and 20 µm at the retina.

Figure 5A:
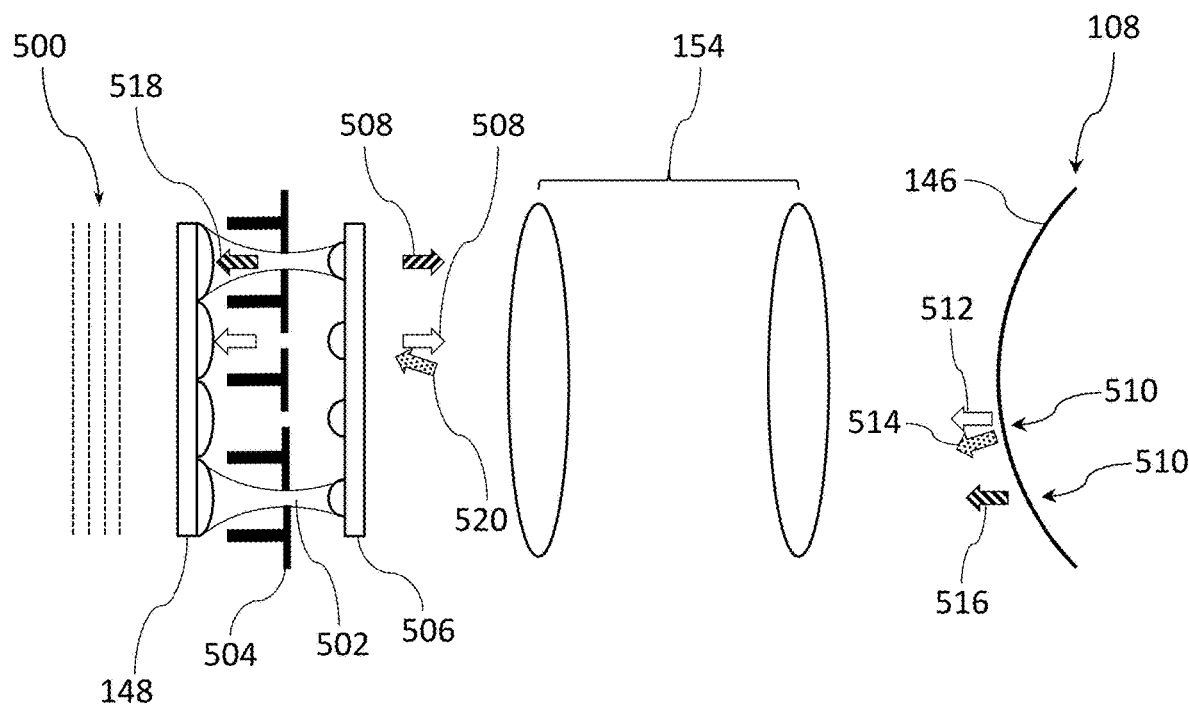
FIG. 5A illustrates in schematic form the sample arm optics of an OCT apparatus, according to another embodiment of the invention.

FIG. 5A shows in schematic form a modification of the sample arm optics of the apparatus 100 shown in FIG. 1A, to provide a spectral domain OCT apparatus according to a third embodiment of the invention. This modification, which can also be applied to the sample arm optics shown in FIG. 4, introduces improved aperturing at the front end of the sample arm to provide better isolation of the returning sample beamlets. As will be explained, this improved aperturing suppresses crosstalk between returning sample beamlets, in particular by suppressing the passage of off-axis high intensity specular reflections. A wavefront 500 in the sample arm is directed towards a spatial sampling element in the form of a 2-D lenslet array 148 that forms a number of beamlets with waists 502 passing through a structured aperturing partition 504 with an aperture dimension comparable to the beam waist or first Rayleigh ring. The beamlets are then relayed by a second 2D lenslet array 506 to provide effective beam waists 508 that can be either in front of or behind the second lenslet array 506 by choice of the separation between the lenslet arrays 148, 506 and the focal length of the second lenslet array. In some cases the focal lengths of the individual lenslets in the second lenslet array 506 can be tailored so that the effective beam waists vary significantly, e.g. to be appropriate for the portions of an eye that are being sampled by the various beamlets. A 4F relay system 154 is provided to relay the effective beam waists towards a sample eye 108. This 4F relay system can be designed such that the size of the sampling points 510 on the eye illuminated by the beamlets is significantly smaller than the separation between them. When a beamlet is relayed to a sampling point 510 on the cornea 146 it will generally produce, in addition to a counter-propagating scattered signal 512, a specular reflected signal 514 that will usually be off-axis, i.e. not counter-propagating. This specular reflection 514 will generally be much stronger than the scattered signal 512 and has the potential to swamp this signal as well as signals 516 scattered from neighbouring sampling points 510 if care is not taken to avoid crosstalk into returning beamlets 518 as they are being conveyed to the detection system. The specular reflected light 514 is transferred by the 4F relay system 154 to a position 520 near to the corresponding effective beam waist 508, and because of its angled path could be directed to a neighbouring lenslet to interfere with its weak scattered signal 518. Such crosstalk could create an error in the identification of an interface or other ocular surface.

Figure 5B:
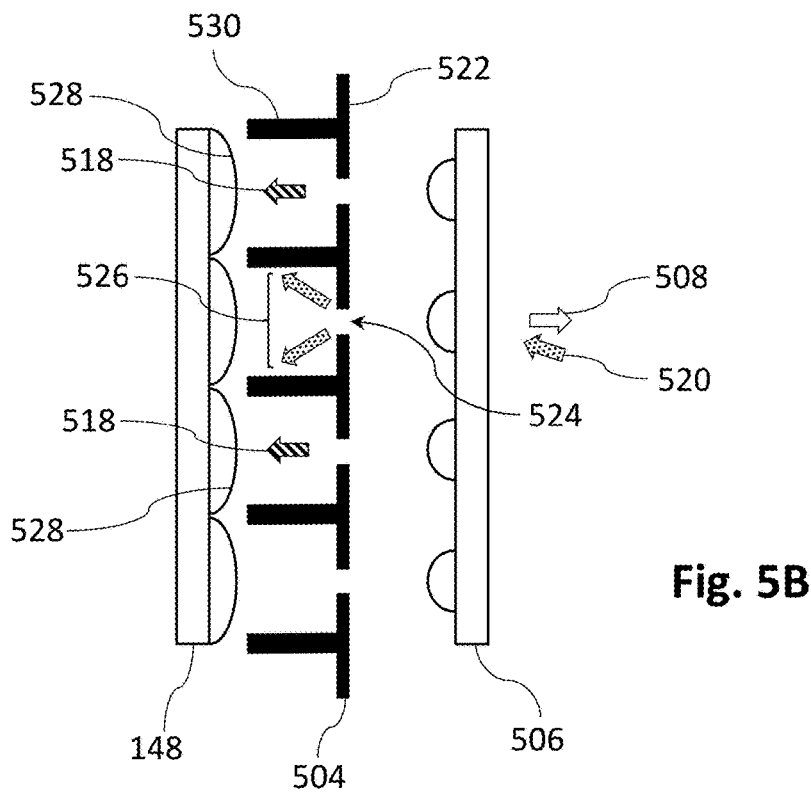
FIG. 5B shows an enlargement of an aperturing portion of the sample arm optics shown in FIG. 5A.

As shown in the enlargement of FIG. 5B, the structured aperturing partition 504 comprises a first member 522 having a plurality of apertures 524 for passing on-axis beamlets 512, 516, 518 returning from the eye. This member 522 will block a significant fraction of the off-axis specular reflection 520 because refraction at the second lenslet array 506 will tend to direct it away from the apertures 524. However a specular reflected beamlet 520 may still clip the edge of an aperture 524, causing diffraction of some of the specular reflected light over a range of angles 526, potentially to be collected by neighbouring lenslets 528 in the first lenslet array 148. To prevent this, the structured aperturing partition 504 preferably includes a second member 530 extending substantially parallel to the propagation direction of the on-axis beamlets 512, 516, 518 for suppressing the passage of off-axis light such as the specular reflections 514, 520. This second member 530, which preferably extends towards the first lenslet array 148, provides additional crosstalk suppression, allowing the weak back-scattered signals 512, 516, 518 to be detected and interpreted more accurately.

The structured aperturing partition 504 may for example be manufacturing by laser drilling apertures 524 into a thin plate to provide the first member 522, with the second member 530 provided by attaching to the plate a honeycomb lattice or similar, with lattice size compatible with the spacing of lenslets in the first lenslet array 148.

Various methods have been described above for creating volume images or tomograms of an eye by registering a plurality of 3-D OCT images or tomograms together to build a composite image, based for example on data from a scleral surface. An additional metrology problem we wish to solve is to be able to provide a 3-D model of the shape of an eye, including the retina, wherein the curvature and shape of the retina can be relied upon, not just the continuity of the image as is the case in most OCT measurements. As mentioned previously, an additional difficulty for using OCT to measure eye shape is that the apparent curvature of the retina is influenced by the position of the OCT instrument relative to the eye. To solve this problem, we further rely upon the information of the relative position of the eye to the instrument as measured by one OCT measurement, together with the knowledge of each of the optical surfaces of the eye as determined by OCT, to allow an accurate reconstruction of the shape of the back surface of the eye. The reconstruction can be based on either:

(i) Complete ray-tracing or other beam propagation simulations using parameters determined from an anterior segment measurement or corrections, wherein the ray-tracing or other optical model provides a calibration between the anterior segment measurement and the converging beamlets of the retinal measurement, together with a calibration of the relative delays of the sample and reference beams; or (ii) The use of a limited set of parameters defining the position of the instrument relative to the eye, say x, y, z and θ, to create a calculated curvature modification to the retinal image, obtained by a formula which accounts for the relative optical trajectories of beamlets through the eye. In both cases it is preferred, but not necessary, for the positional information of the instrument relative to the eye to be acquired simultaneously with the retinal images.

We have also found that the posterior iris surface 1204, clearly visible in FIG. 12 for example, provides a relatively smooth and well-defined surface that can in certain cases be an appropriate reference surface for registering a plurality of OCT frames or images. However in such cases when an interior surface is used as a reference, rather than an exterior surface such as the anterior sclera, the absolute position of the eye needs to be calculated by taking account of the optical refractions that have occurred prior to that interior surface in a self-consistent fashion.

In certain embodiments a full optical model of the front of the eye, e.g. anterior and posterior corneal topography, will have been generated previously with the instrument in a different acquisition mode and potentially using a different delay and/or instrument position.

Figure 15:
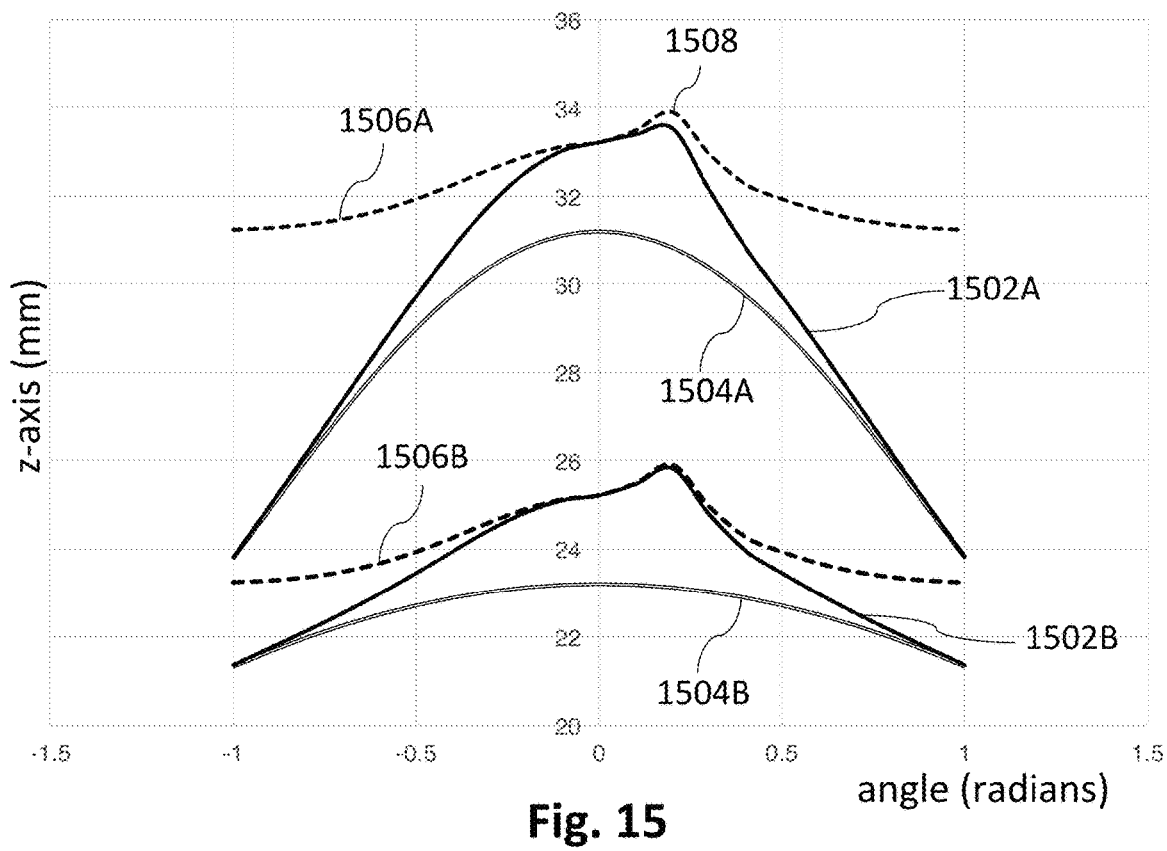
FIG. 15 illustrates the use of classical geometrical optics to ascertain the apparent shape of the retina as a function of instrument position, to allow correction of the influence of the position of an OCT instrument relative to the eye.

FIG. 15 illustrates schematically a simplified simulated example of case (ii) above, i.e. of using classical geometrical optics to ascertain either the apparent or actual shape of the retina as a function of instrument position, represented as angle from the corneal apex. The solid lines 1502A and 1502B show the measured distance in mm to the retina, relative to a specific interface that can be determined from the A-scans, for two different axial instrument positions. These lines represent the apparent retinal shape for the different axial instrument positions. The double lines 1504A and 1504B correspond to the apparent shape of a perfectly spherical retinal surface of radius R, determined from the measured properties of the anterior segment of the eye. The dashed lines 1506A and 1506B now show the calculated shape of the retina relative to the sphere of radius R. The location of the fovea is illustrated schematically by the dip 1508 in the retinal shape. It can be seen that the calculated shape of the retina relative to the sphere of radius R is independent of the axial position of the instrument relative to the eye, demonstrating correction of the apparent retinal shape. Although for simplicity the example here only shows a variation of the axial position of the instrument, in this case of approximately 8 mm, the angular orientation and lateral position of the instrument with respect to the eye can be accounted for in a similar way to ensure that a repeatable and accurate measurement of retinal shape can be acquired.

Figure 16:
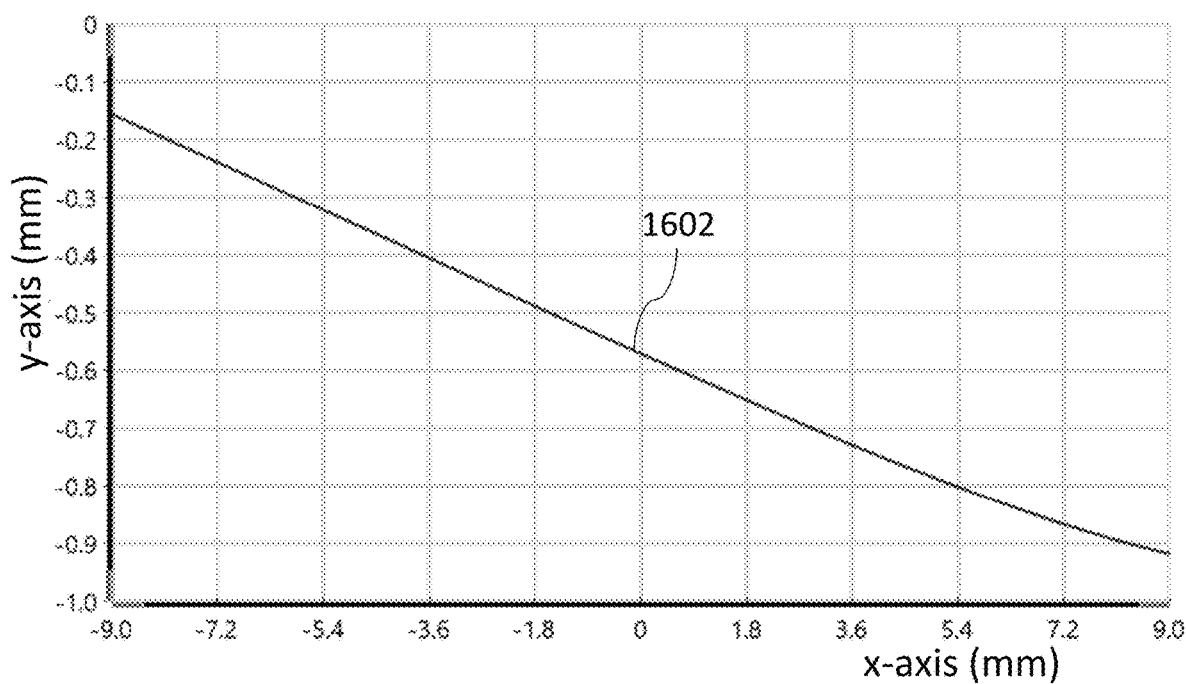
FIG. 16 shows a correction term for axial depth, as calculated using a ray trace algorithm, for correcting retinal shape for variations in instrument position.

As an example of case (i) above, FIG. 16 shows a correction term 1602 for axial depth, for a particular angular position on the eye, as calculated using a ray trace algorithm. In this graph the x-axis represents eye position, i.e. relative distance away from the design corneal plane in mm, while the y-axis represents the maximum difference in optical path length, in mm, between an on-axis beamlet and an off-axis beamlet. The correction is determined based on the measured parameters of the anterior segment of the eye and the relative position of the eye to the instrument, with a lens configuration suitable for measuring the retina in place.

Figure 17:
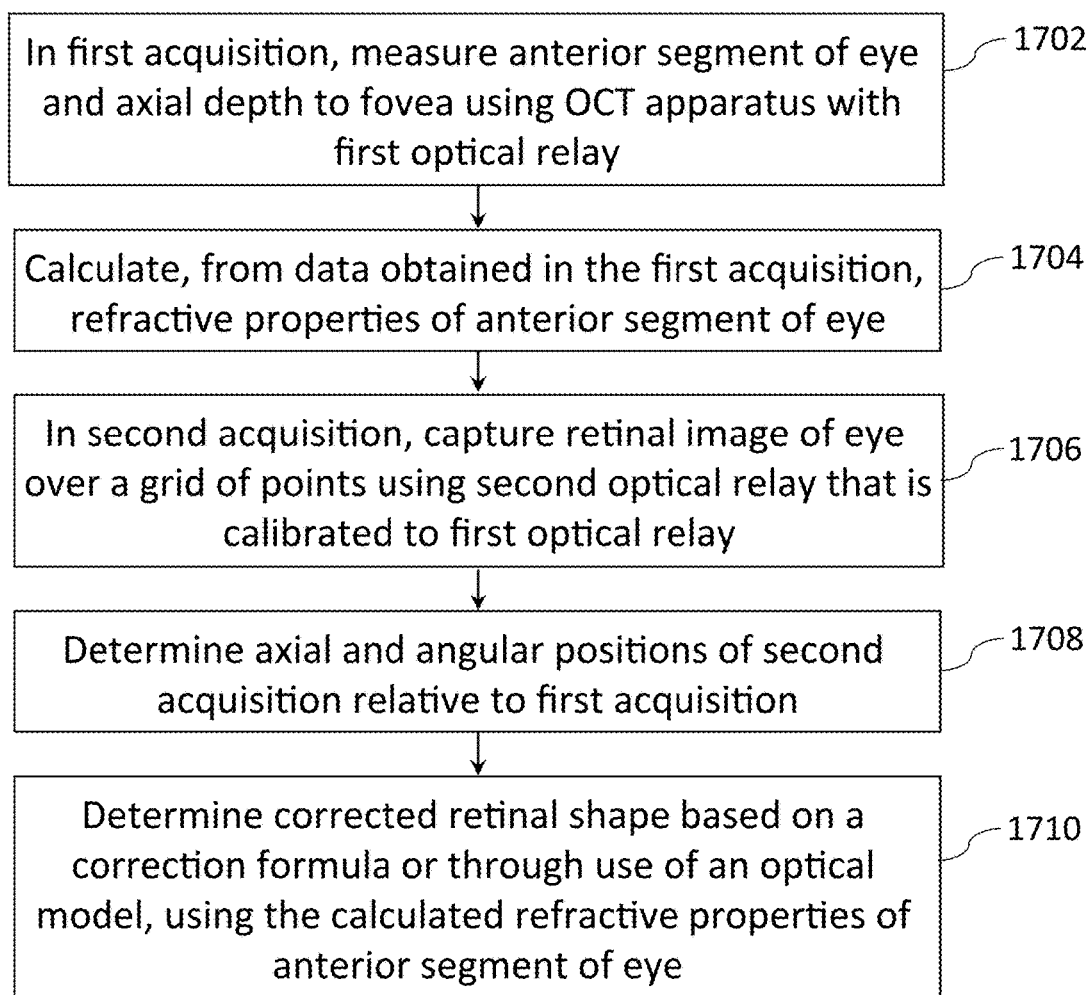
FIG. 17 depicts a flow chart for determination of an improved measure of eye shape, with correction of the influence of instrument position relative to the eye.

FIG. 17 depicts a flow chart for determination of an improved measure of eye shape according to a preferred embodiment, with correction of the influence of instrument position relative to the eye. In step 1702 the anterior segment of a sample eye, along with axial depth to the fovea, are measured in a first acquisition, using an OCT apparatus with a first optical relay such as the 4F lens system 154 shown in the sample arm of FIG. 1A. Preferably, the axial depth is measured to the retinal pigment epithelium (RPE) at the fovea. Refractive properties of the anterior segment of the eye are then calculated in step 1704, from data obtained in the first acquisition. In step 1706 a retinal image of the eye is captured over a grid of points in a second acquisition, using a second optical relay such as the relay system 400 shown in FIG. 4, that is calibrated relative to the first optical relay. This enables the relative axial and angular positions of the first and second acquisitions to be determined in step 1708. Finally in step 1710 the corrected retinal shape is determined, for example based on a correction formula as discussed regarding FIG. 15 or through use of a ray-tracing or other optical model for beam propagation as discussed regarding FIG. 16. We note that the axial eye depth measured in step 1702 does not necessarily have to be the depth to the fovea, but it is convenient to align to the fovea using a fixation target. The fovea can also be identified from the retinal image captured in step 1706.

Although in the preceding discussion we have described metrology and tomography with registration of retinal or other internal ocular data using data from an anterior surface of the eye, such as the anterior sclera or the posterior iris surface, it is possible that in a system with simplified hardware only retinal data is available. For example there may be no registration points provided by the peripheral beamlets 410 as shown in FIG. 4. In this case we can rely on the morphology of the eye to provide an additional marker for identification of the axial position. If we only have the axial lengths as a function of the angular spread of beamlets, e.g. from the on-retina positions 422 of central beamlets 416 as shown in FIG. 4, but had previously acquired a full anterior segment and the foveal length, that will be sufficient in many cases to define the problem and correct the axial lengths for instrument position. The distance between the instrument and the eye would be known, but without the angular content the correction may not be straightforward. However with identification of the fovea the correction is possible, through the morphology of the eye, with no further registration required. This solution is susceptible to accommodation change, although there are cases where this can be well controlled, e.g. with pupil dilation or a fixation target. In this instance, with the retinal beamlets 416 creating a wide, dense grid of scan points 422 on the retina 144, it is possible to achieve registration of each of the grid points purely on the basis of the shape of the eye. For example for an eye with a given foveal depth we can predict the apparent shape of an assumed spherical retinal surface. The deviations from that predicted shape represent the real shape variation of the eye, which is a smooth enough function with sufficient features to allow each grid of snap-shots to be aligned. For a low-cost instrument that uses a 4F relay 154 with single focal length lenses in the sample arm optics for both anterior and retinal measurements, and potentially without requiring a multi-length delay element such as a compound reflector 110, this is an attractive alternative. The location of the fovea can be determined either through identification of the foveal dip in the depth mapping, as shown in FIG. 15 for example, or through the use of an integrated retinal camera that is angularly registered to the OCT instrument.

In the optical coherence tomography apparatus depicted in FIG. 1A, a multi-length delay element in the form of a compound reflector 110 is located in the reference arm, for imposing a predetermined optical path length difference on laterally separated portions 134, 138 of the reference beam 122. This enables single shot acquisition of interferometric data from a number of axially separated regions of a sample such as an eye, thereby extending the depth of field of the apparatus. A similar effect can be achieved with a transmissive element located in the sample arm, with the interferometer configured such that the sample beam passes through the element either before and after interacting with a sample, or only before or only after interacting with a sample.

Figure 18A:
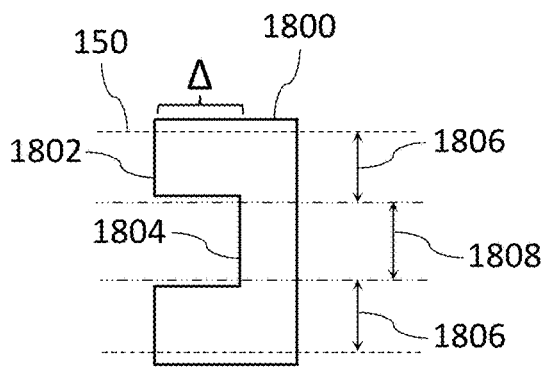
FIGS. 18A and 18B show in schematic form two variants of a transmissive multi-length delay element for imposing a differential delay on different portions of a sample beam or array of sample beamlets.

FIG. 18A depicts schematically a transmissive multi-length delay element 1800 composed of a piece of glass or other transparent material of refractive index n(λ) and having a first, outer section 1802 that is thicker than a second, inner section 1804 by an amount A. If light in a sample beam 150 passes through the element 1800 both before and after interacting with a sample, as it would when the element is located in the sample arm of the ocular OCT apparatus shown in FIG. 1A, a first, outer portion 1806 of the sample beam will receive a delay that is greater than the delay received by a second, inner portion 1808 by an amount equal to 2⊕Δ⊕n(λ). This is an equivalent effect to that provided by the reference arm compound reflector 110 shown in FIG. 1A, enabling for example single shot acquisition of interferometric data from the anterior sclera 106 and the retina 144 using the outer and inner portions 1806, 1808 of the sample beam 150. It will be appreciated that the inner section 1804 of the element 1800 could be dispensed with, in which case the element may be an annular piece of glass of thickness Δ. As before, the material of the element 1800 may be chosen to have a dispersion that at least partially compensates for the dispersion of the eye, and the element can be moved out of the sample beam path if the differential delay is not required. With reference to FIG. 1A, the element 1800 may for example be placed between the quarter wave plate 156 and the lenslet array 148. Alternatively, it may be located between the lenslet array 148 and the 4F lens system 154, in which case a predetermined optical path length difference will be imposed on separate subsets of the array of sample beamlets 152.

Figure 18B:
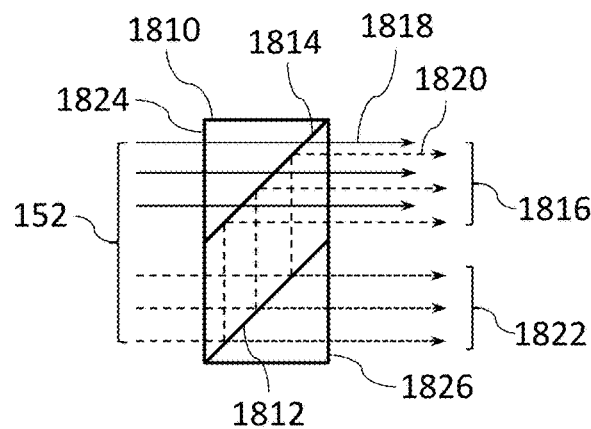

FIG. 18B depicts schematically another transmissive multi-length delay element 1810 for imposing a predetermined optical path length difference on various subsets of an array of sample beamlets 152, or equivalently on different portions of a sample beam. In one embodiment the element 1810 comprises a beamsplitter with a first, fully reflective angled surface 1812 and a second, partially reflective angled surface 1814. In combination these angled surfaces serve to convert an array of sample beamlets 152, produced for example with a lenslet array (not shown), into a multiplexed set of beamlets 1816 in which some beamlets 1818 have traysersed a shorter optical path length than other beamlets 1820. With reference to FIG. 1A, the multiplexed set of beamlets 1816 could be useful for example for obtaining interference signals from both the cornea 146 and the retina 144. In another embodiment the first angled surface 1812 is partially reflective, for providing a separate subset of beamlets 1822 with the same optical delay as the beamlets 1818. In yet another embodiment the first angled surface 1812 is partially reflective and the second angled surface 1814 fully reflective, for providing laterally spaced apart subsets of beamlets 1820, 1822 having different optical delays, for obtaining interferometric signals from the anterior sclera 106 and retina 144 for example. It still other embodiments the first and second angled surfaces 1812, 1814 have polarisation-dependent reflectivity, enabling the optical path length of various beamlets to be tailored via polarisation control, e.g. with appropriately positioned polarising layers on the front or back surfaces 1824, 1826 of the element 1810, or with external polarisers.

It will be appreciated that an OCT apparatus could alternatively be configured to have a transmissive multi-length delay element such as the element 1800 in the reference arm, or a reflective multi-length delay element such as the compound reflector 110 in the sample arm, again for imposing a predetermined optical path length difference on laterally spaced portions of a reference beam or a sample beam.

In FIG. 1A the compound reflector 110 is a component of a spectral domain OCT apparatus designed for single shot measurement of various structures in an eye 108 across a 2-D grid of points. The eye is probed with a 2-D array of beamlets 152, and the returning beamlets interfered with a reference beam 122 and dispersed onto separate sets of pixels of a 2-D sensor array 178 for detection and subsequent processing. However it will be appreciated that a compound reflector or other form of multi-length delay element could also be used to extend the depth of field of other types of OCT apparatus, or for investigating non-ocular samples over an extended axial depth range. In one example a compound reflector could be placed in the reference arm of a scanning spot spectral domain OCT apparatus in which interferometric signals from a sequence of spots on a sample are dispersed onto a 1-D sensor array for sequential read out and processing. The predetermined optical path length difference imposed on different portions of the reference beam serves to at least partially compensate for the axial separation between various structures of a sample, either within a single frame or in different frames. In another example a compound reflector could be placed in the reference arm of a swept source OCT apparatus to extend the depth range over which interferometric signals can be measured with a point detector as a tuneable or steppable optical source is scanned in wavelength.

Although the invention has been described with reference to specific examples, it will be appreciated by those skilled in the art that the invention may be embodied in many other forms.

The invention claimed is:

1. A method for performing optical coherence metrology or tomography of a sample, said method comprising the steps of:
  (i) splitting light from an optical source into a sample beam and a reference beam;
  (ii) imposing a predetermined optical path length difference on first and second laterally spaced portions of said sample beam or on first and second laterally spaced portions of said reference beam;
  (iii) directing said sample beam onto said sample for interaction with first and second regions of said sample that are axially separated and laterally spaced, and collecting light reflected from or transmitted through the first and second axially separated and laterally spaced regions of said sample;
  (iv) mixing said reference beam with the reflected or transmitted light;
  (v) detecting an interference signal resulting from the mixing of the reference beam with the reflected or transmitted light; and
  (vi) processing the detected interference signal to provide an optical coherence tomogram of said sample,
  wherein said predetermined optical path length difference at least partially compensates for the axial separation between the first and second regions of said sample.

2. The method according to claim 1, wherein said sample beam comprises an array of beamlets for interaction with a plurality of discrete points within the first or second regions of said sample.

3. The method according to claim 1, wherein said predetermined optical path length difference is imposed on first and second laterally spaced portions of said reference beam.

4. The method according to claim 3, wherein said predetermined optical path length difference is imposed by a compound reflector having first and second axially separated reflective surfaces for reflecting the first and second laterally spaced portions of said reference beam.

5. The method according to claim 1, wherein said sample comprises an eye.

6. A non-transitory computer readable medium with an executable program code configured to implement the method according to claim 1.

7. An apparatus for performing optical coherence metrology or tomography of a sample, said apparatus comprising:

an optical source;

an interferometer for:

splitting light from said optical source into a sample beam and a reference beam;

directing said sample beam onto a sample for interaction with first and second regions of said sample that are axially separated and laterally spaced, and collecting light reflected from or transmitted through the first and second axially separated and laterally spaced regions of said sample; and mixing said reference beam with the reflected or transmitted light;

a detector for detecting an interference signal resulting from the mixing of the reference beam with the reflected or transmitted light;

a multi-length delay element for imposing a predetermined optical path length difference on first and second laterally spaced portions of said sample beam or on first and second laterally spaced portions of said reference beam; and a computer for processing the detected interference signal to provide an optical coherence tomogram of said sample, wherein said multi-length delay element is selected such that said predetermined optical path length difference at least partially compensates for the axial separation between the first and second regions of said sample.

8. The apparatus according to claim 7, comprising a spatial sampling element for generating from said sample beam an array of beamlets for interaction with a plurality of discrete points within the first or second regions of said sample.

9. The apparatus according to claim 8, wherein said spatial sampling element comprises a lenslet array.

10. The apparatus according to claim 7, wherein said multi-length delay element is configured to impose said predetermined optical path length difference on first and second laterally spaced portions of said reference beam.

11. The apparatus according to claim 10, wherein said multi-length delay element comprises a compound reflector having first and second axially separated reflective surfaces for reflecting the first and second laterally spaced portions of said reference beam.

12. The apparatus according to claim 7, wherein said multi-length delay element comprises a medium selected to have a dispersion that at least partially compensates for the dispersion of said sample.

13. The apparatus according to claim 7, wherein said apparatus is configured for performing optical coherence metrology or tomography of an eye.

14. The apparatus according to claim 13, wherein said first region is in the anterior segment of said eye and said second region is in the posterior segment of said eye.

15. The apparatus according to claim 14, wherein said first region comprises the anterior sclera of said eye.

16. The apparatus according to claim 15, wherein said second region comprises the fovea of said eye.

17. The apparatus according to claim 14, wherein said second region comprises the fovea of said eye.

18. A non-transitory computer readable medium with an executable program code configured to operate the apparatus according to claim 7.

19. An apparatus for performing optical coherence metrology or tomography of an eye, said apparatus comprising:

an optical source;

an interferometer for:

splitting light from said optical source into a sample beam and a reference beam;

directing said sample beam onto an eye for interaction with first and second regions of said eye that are axially separated and laterally spaced, and collecting light reflected from or transmitted through the first and second axially separated and laterally spaced regions of said eye; and mixing said reference beam with the reflected or transmitted light;

a detector for detecting an interference signal resulting from the mixing of the reference beam with the reflected or transmitted light;

a multi-length delay element for imposing a predetermined optical path length difference on first and second laterally spaced portions of said sample beam or on first and second laterally spaced portions of said reference beam; and a computer for processing the detected interference signal to provide an optical coherence tomogram of said eye, wherein said multi-length delay element is selected such that said predetermined optical path length difference at least partially compensates for the axial separation between the first and second regions of said eye.

20. A non-transitory computer readable medium with an executable program code configured to operate the apparatus according to claim 19.

* * * * *